United States Patent
Cooper-White et al.

(10) Patent No.: US 10,494,453 B2
(45) Date of Patent: Dec. 3, 2019

(54) CONJUGATE COMPOUND AND USES OF SAME

(71) Applicant: THE UNIVERSITY OF QUEENSLAND, St. Lucia (AU)

(72) Inventors: Justin Cooper-White, Upper Brookfield (AU); Peter Ghosh, Melbourne (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 10 days.

(21) Appl. No.: 14/768,474

(22) PCT Filed: Feb. 20, 2014

(86) PCT No.: PCT/AU2014/000150
§ 371 (c)(1),
(2) Date: Aug. 18, 2015

(87) PCT Pub. No.: WO2014/127418
PCT Pub. Date: Aug. 28, 2014

(65) Prior Publication Data
US 2016/0002366 A1    Jan. 7, 2016

(30) Foreign Application Priority Data
Feb. 20, 2013  (AU) ............................... 2013900622

(51) Int. Cl.
| | | |
|---|---|---|
| *A61K 31/728* | (2006.01) | |
| *A61K 31/737* | (2006.01) | |
| *A61K 35/28* | (2015.01) | |
| *C08B 37/08* | (2006.01) | |
| *A61K 35/32* | (2015.01) | |
| *A61K 35/12* | (2015.01) | |
| *A61K 45/06* | (2006.01) | |
| *C08B 37/00* | (2006.01) | |
| *A61K 47/55* | (2017.01) | |
| *A61K 47/61* | (2017.01) | |

(52) U.S. Cl.
CPC ........ *C08B 37/0072* (2013.01); *A61K 31/728* (2013.01); *A61K 31/737* (2013.01); *A61K 35/12* (2013.01); *A61K 35/28* (2013.01); *A61K 35/32* (2013.01); *A61K 45/06* (2013.01); *A61K 47/55* (2017.08); *A61K 47/61* (2017.08); *C08B 37/0057* (2013.01)

(58) Field of Classification Search
CPC ... A61K 2300/00; A61K 31/728; A61K 35/38
See application file for complete search history.

(56) References Cited

U.S. PATENT DOCUMENTS

| | | | | |
|---|---|---|---|---|
| 5,470,911 A | * | 11/1995 | Rhee ...................... | C09J 189/06 525/54.1 |
| 7,582,311 B1 | * | 9/2009 | Cleland ................ | A61K 9/0019 424/488 |
| 2004/0142465 A1 | * | 7/2004 | Radice ................... | A61L 27/20 435/372 |
| 2009/0048147 A1 | * | 2/2009 | Holmes .............. | C07D 207/452 514/1.1 |
| 2009/0093414 A1 | * | 4/2009 | Ikeya ................... | A61K 31/519 514/4.8 |
| 2010/0168228 A1 | * | 7/2010 | Bose .................... | A61K 31/216 514/469 |
| 2011/0212914 A1 | * | 9/2011 | Ellinghuysen ....... | A61K 9/0019 514/54 |
| 2012/0196830 A1 | * | 8/2012 | Parsons ................ | A61K 9/0034 514/56 |
| 2013/0017232 A1 | | 1/2013 | Varghese et al. | |

FOREIGN PATENT DOCUMENTS

| | | | |
|---|---|---|---|
| EP | 0296740 A2 * | 12/1988 | ......... A61K 47/4823 |
| WO | 2002/100453 | 12/2002 | |
| WO | 2012/027797 | 3/2012 | |

OTHER PUBLICATIONS

ThermoFisher Scientific. Overview of Crosslinking and Protein Modification. Date Retrieved: Dec. 12, 2017. (Year: 2017).*
Lupia et al. Pentosan polysulfate inhibits atherosclerosis in Watanabe heritable hyperlipidemic rabbits: differential modulation of metalloproteinase-2 and -9. Laboratory Investigation. (2012). vol. 92. pp. 236-245. (Year: 2012).*
Helmenstine, Anne Marie. Ionic vs Covalent Bonds—Understand the Difference. Jan. 24, 2019. ThoughtCo. <https://www.thoughtco.com/ionic-and-covalent-chemical-bond-differences-606097>. (Year: 2019).*
Frith et al. "Effects of bound versus soluble pentosan polysulphate in PEG/HA-based hydrogels tailored for intervertebral disc regeneration" *Biomaterials*, vol. 35, No. 4, pp. 1150-1162 (Jan. 2014).
International Search Report for PCT/AU2014/000150, four pages, dated Apr. 3, 2014.

* cited by examiner

*Primary Examiner* — Tracy Liu
(74) *Attorney, Agent, or Firm* — Nixon & Vanderhye P.C.

(57) ABSTRACT

Conjugate compounds of hyaluronic acid bonded to pentosan polysulfate, or salts or derivatives thereof, are shown to induce chondrogenic differentiation of a population of mesenchymal stem cells as observed by, amongst other indications, increased glycosaminogSycan (GAG) production.

19 Claims, 11 Drawing Sheets

CONJUGATE COMPOUND AND USES OF SAME

This application is the U.S. national phase of International Application No. PCT/AU2014/000150, filed 20 Feb. 2014, which designated the U.S. and claims priority to Application No. AU 2013900622, filed 20 Feb. 2013; the entire contents of each of which are hereby incorporated by reference.

FIELD OF THE INVENTION

The invention relates to the field of medical treatment. More particularly, this invention relates to a novel conjugate compound and its use in treating or preventing a disease or condition responsive to connective tissue repair and/or maintenance.

BACKGROUND TO THE INVENTION

Any reference to background art herein is not to be construed as an admission that such art constitutes common general knowledge in Australia or elsewhere.

Adult mesenchymal stem cells (MSCs) are an abundant source of self-renewing, multipotent undifferentiated cells that can be readily isolated from bone marrow, adipose tissue, muscle and synovium, and expanded in ex vivo culture. The ability of these cells to differentiate into bone, cartilage, adipose, tendon and other cells of the mesenchymal lineage under appropriate stimuli offers the potential for the regeneration and repair of the musculoskeletal system by their direct application to sites of injury [1-3] or by their incorporation into bioscaffolds and transplantation into the sites of the tissue defect [1,4,5].

Stromal tissue in the bone marrow consists of a heterogeneous population of MSCs that occupy a perivascular niche. Studies have provided evidence for the existence within this niche of smaller precursor stem cell populations that exhibit extensive proliferative and multilineage differentiative capacity and can be distinguished by their expression of certain cell surface antigens [6,7]. These undifferentiated mesenchymal precursor cells (MFCs) can be isolated from bone marrow aspirates using techniques such as magnetic activated cell sorting in combination with antibodies that identify STRO-1, VCAM-1 (CD106), STRO-3 (tissue nonspecific alkaline phosphatase), STRO-4 (HSP-90b) and CD146 [6,7].

Using this approach, a homogeneous population of quiescent MPCs can be obtained that lack the phenotypic characteristics of leukocytes and mature stromal elements and exhibit extensive proliferative capacity while retaining the ability to differentiate into bone, cartilage and adipose tissues.

WO 2009/018613 in the name of Angioblast Systems Inc disclosed the use of MPCs in treating diseases with an underlying etiology of inflamed or degraded connective tissue such as, for example, degenerative cervical and lumbar disc conditions. The intra-articular administration of MPCs was described as providing a chondroprotective effect in joints with pre-existing osteoarthritis and was found to lead to the growth of cartilage tissue in synovial joints and the nucleus pulposus of intervertebral discs.

Ghosh et al [8] demonstrated that the presence of the semi-synthetic sulphated polysaccharide, pentosan polysulfate (PPS), induced the in vitro proliferation and chondrogenic differentiation of MPCs even absent the addition of growth factors or other chondroinductive supplements. It was postulated that a treatment regime combining PPS with MPCs could benefit patients requiring repair and reconstitution of injured and degenerate cartilaginous tissues. The specificity of PPS as a promoter of chondrogenesis and the unpredictability of the success of other polysaccharides was demonstrated by the fact that dextran sulphate and heparin did not show any success in this role while hyaluronan showed some stimulation of MPCs to synthesis proteoglycan (PG) when present at low concentrations but at higher concentrations actually inhibited PG synthesis.

The use of MPCs, with or without a promoter such as PPS, opens up a wide range of potential treatment methodologies to address diseases or conditions resulting from degradation of cartilaginous tissues. Intervertebral disc (IVD) degeneration is just such a condition which can cause great discomfort and reduce quality of life significantly for a sufferer. Current treatments include immobilization and surgical intervention. Neither approach actually repairs the underlying tissue degeneration and recurrence of symptoms is likely.

MPCs thus present the possibility of a new treatment paradigm. However, their use will require both effective delivery and careful control of the chemical and physical cues provided to ensure appropriate differentiation to provide regenerated or repaired tissue.

OBJECT OF THE INVENTION

It is an aim of this invention to provide for a conjugate compound suitable for treating a condition responsive to connective tissue repair and/or maintenance which overcomes or ameliorates one or more of the disadvantages or problems described above, or which at least provides a useful alternative.

Other preferred objects of the present invention will become apparent from the following description.

SUMMARY OF INVENTION

According to a first aspect of the invention, there is provided a conjugate compound comprising hyaluronic acid, or a salt or derivative thereof, bonded to pentosan polysulfate, or a salt or derivative thereof.

Preferably, the hyaluronic acid and pentosan polysulfate are covalently bonded.

Suitably, the conjugate compound is of formula HA-L-PPS wherein HA is hyaluronic acid, or a salt or derivative thereof, PPS is pentosan polysulfate, or a salt or derivative thereof, and L is a linker unit having a first reactive group reactive with a first complimentary group on hyaluronic acid and further having a second reactive group reactive with a second complimentary group on pentosan polysulfate.

Preferably, L has a first reactive group reactive with a carbonyl or hydroxyl functional group on hyaluronic acid.

Suitably, L has a second reactive group reactive with a carboxylic acid group on pentosan polysulfate.

Preferably, the first and second reactive group are selected from the group consisting of —$NH_2$, OH and H.

In one embodiment, the conjugate compound of the first aspect is a conjugate compound of formula (I), or a salt thereof:

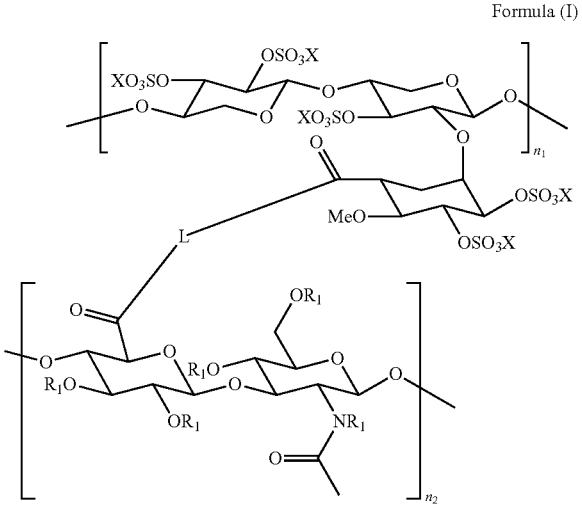

Formula (I)

wherein, $n_1$ is sufficient to provide a molecular weight of between 1,000 to 20,000 daltons for the pentosan polysulfate component of the conjugate and $n_2$ is sufficient to provide a molecular weight of between 5,000 to 20,000,000 daltons for the hyaluronic acid component of the conjugate;

each X is independently a salt forming ion selected from the group consisting of sodium, calcium, magnesium and potassium ions OR X may be selected from hydrogen, alkyl, alkenyl, carboxyl, alkanoyl, alkanoyloxy and carboalkoxy;

each $R_1$ group is independently selected from a salt forming ion, hydrogen, alkyl, alkenyl, arylalkyl, hydroalkyl, aldehyde, alkanone, carboxyl, carboxamide, alkanoyl, carboalkoxy, carboaryloxy, carbonate, O-alkyl, O-aryl, O-alkenyl, O-alkanoyl and O-alkenoyl; and L is a linker unit as described above.

Preferably, $n_1$ is sufficient to provide a molecular weight of between 2000 to 10,000 daltons, more preferably 4000 to 8000, for the pentosan polysulfate component of the conjugate.

Preferably, $n_2$ is sufficient to provide a molecular weight of between 50,000 daltons to 2,000,000 daltons, more preferably between 100,000 daltons to 500,000 daltons for the hyaluronic acid component of the conjugate.

Preferably, L is $R_2$ which is selected from alkyl, aminoalkyl, diaminoalkyl, acyl, ether each of which may contain one or more further heteroatoms selected from sulphur, oxygen and nitrogen In one preferred embodiment the conjugate compound of formula (I) is a conjugate compound of formula (II), or a salt thereof:

Formula (II)

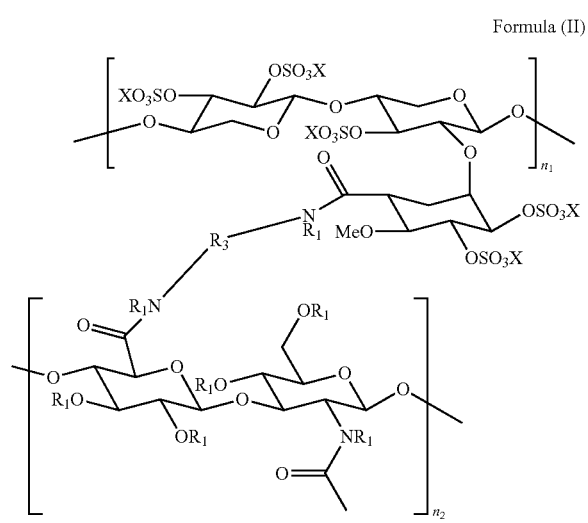

wherein X, $R_1$, $n_1$ and $n_2$ are as already described and wherein, $R_3$ is selected from alkyl, disulphide, alkyldisulphide, acyl, ether, carboalkoxy and alkanoyloxy.

In one highly preferred embodiment the conjugate compound of formula (I) is a conjugate compound of formula (III), or a salt thereof:

Formula (III)

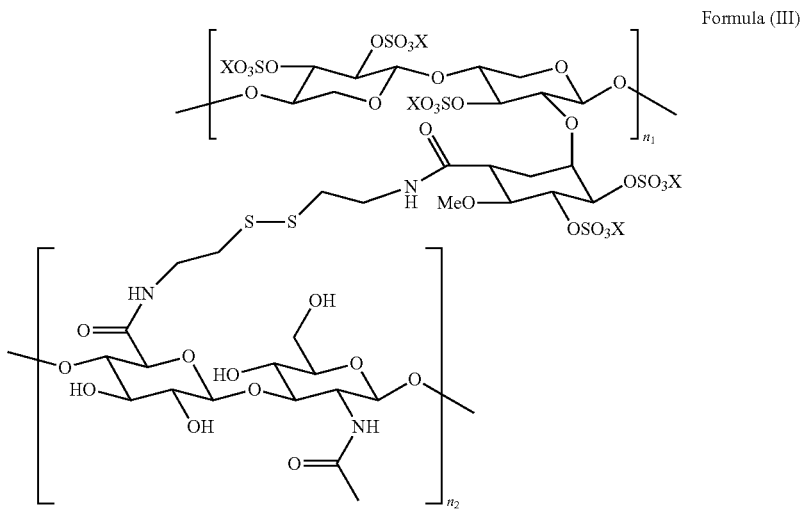

wherein $n_1$ and $n_2$ and X are as already described.

Preferably, X is sodium,

In a further highly preferred embodiment the conjugate compound of formula (I) is a conjugate compound of formula (IIIa), or a salt thereof:

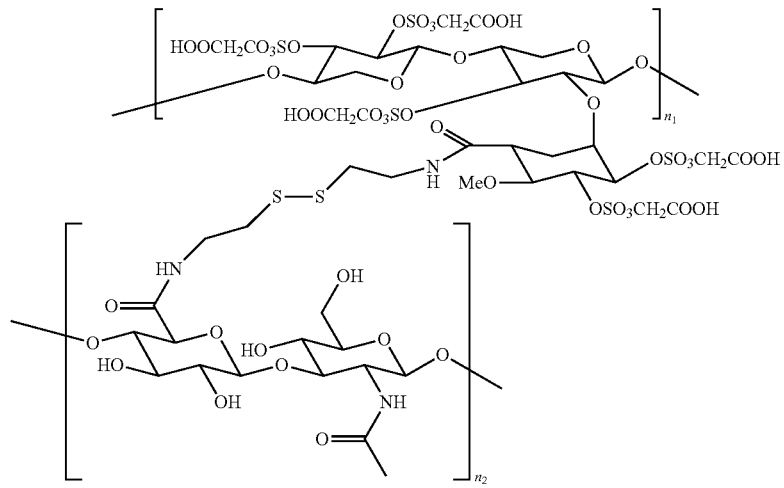

wherein $n_1$ and $n_2$ are as defined above.

According to a second aspect of the invention there is provided a method of synthesising a conjugate compound of the first aspect including the step of coupling hyaluronic acid, or a derivative thereof, to pentosan polysulfate, or a derivative thereof, via a covalent bond.

Preferably, the hyaluronic acid or pentosan polysulphate, or a salt or derivative thereof, are first chemically modified to present a linker unit prior to covalent bonding.

Suitably, the hyaluronic acid, or salt or derivative thereof, is chemically modified to present a linker group having a primary amine functionality.

Preferably, the chemical modification of the hyaluronic acid, or salt or derivative thereof, is performed via a carboxyl group activation pathway using a carboxyl activating group. Preferably, the carboxyl activating group is an imide, more preferably it is a carbodiimide such as 1-ethyl-3-(3-dimethylaminopropyl) carbodiimide (EDC), and/or a succinimide such as N-hydroxysuccinimide ester Suitably, the primary amine of the hyaluronic acid linker group is reacted with a carboxyl group on the pentosan polysulfate, or salt or derivative thereof.

A third aspect of the invention resides in a conjugate compound produced by the method of the second aspect.

According to a fourth aspect of the invention there is provided a pharmaceutical composition comprising an effective amount of a conjugate compound of the first or third aspect, or a pharmaceutically acceptable salt thereof, and a pharmaceutically acceptable carrier, diluent and/or excipient.

Suitably, the pharmaceutical composition is for the treatment or prophylaxis of a disease, disorder or condition responsive to connective tissue repair and/or maintenance, such as connective tissue degeneration.

In one embodiment, the pharmaceutical composition further comprises pluripotent or multipotent stem cells. In one particular embodiment, the pharmaceutical composition may take the form of a polymeric matrix within which the conjugate compound of the first or third aspect and a multipotent stem cell population are located. Preferably, the polymeric matrix is a hydrogel.

The pharmaceutical composition may comprise further additives selected from the group consisting of glycosaminoglycan (GAG), unbound hyaluronic acid (HA), chondroitin sulphate, dermatan sulphate, keratin sulphate, heparin, heparin sulphate and unbound PPS.

A fifth aspect of the invention resides in a method of treating or preventing a disease, disorder u condition responsive to connective tissue repair and/or maintenance in a patient including the step of administering an effective amount of a conjugate compound of the first or third aspect and pluripotent or multipotent stem cells, and/or progeny cells thereof, or the pharmaceutical composition of the fourth aspect to the affected or potentially affected tissue.

In one embodiment, the disease, disorder or condition is connective tissue degeneration. Preferably, the affected tissue is an intervertebral disc, a cartilaginous structure, such as a meniscus, or bone tissue.

The conjugate compound and multipotent stem cells may be co-administered. Preferably, the conjugate compound and multipotent stem cells are administered within a polymeric matrix, such as a hydrogel.

The multipotent stem cells may be selected from the group consisting of mesechymal precursor cells (MPCs), dental pulp stem cells (DPSCs) and periodontal ligament stem cells (PDLSCs).

Preferably, the multipotent stem cells are MPCs. In one embodiment, the MPCs are STRO-1$^+$ MPCs. In a particular embodiment, the MPCs are obtained or are obtainable from human bone marrow.

The method may also include administering further additives selected from the group consisting of glycosaminoglycan (GAG), unbound hyaluronic acid (HA), chondroitin sulphate, dermatan sulphate, keratin sulphate, heparin, heparin sulphate and unbound PPS.

A sixth aspect of the invention provides for a conjugate compound of the first or third aspect, or a pharmaceutically acceptable salt thereof, for use in the treatment or prophylaxis of a disease, disorder or condition responsive to connective tissue repair and/or maintenance in a patient.

A seventh aspect of the invention resides in a method of enhancing, promoting or maintaining the chondrogenic potential of a stem cell including the step of contacting the stem cell with the conjugate compound of the first or third aspect. The stem cell may be selected from the group consisting of MPCs, DPSCs and PDLSCS.

An eighth aspect of the invention resides in a method of reducing or inhibiting the osteogenic differentiation of a stem cell including the step of contacting the stem cell with the conjugate compound of the first or third aspect. The stem cell may be selected from the group consisting of MPCs, DPSCs and PDLSCs.

A ninth aspect of the invention resides in the use of the conjugate compound of the first or third aspects in the manufacture of a medicament for the treatment or prophylaxis of a disease, disorder or condition responsive to connective tissue repair and/or maintenance.

The various features and embodiments of the present invention, referred to in individual sections above apply, as appropriate, to other sections, *mutatis mutandis*. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein:

FIG. 58 is a proton NMR spectrum of HA-PPS$_{COOH}$;

DETAILED DESCRIPTION

Figure 1:
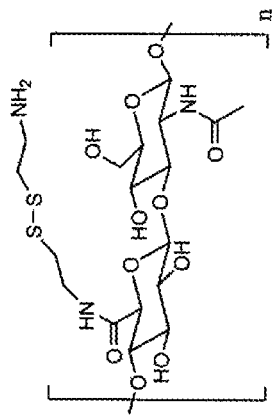
FIG. 1 is a reaction scheme for the functionalisation of HA to present a linker unit.
Figure 1:
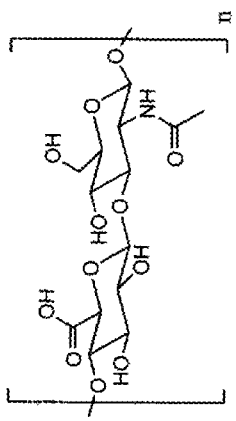

The present invention is predicated, at least in part, on the finding that a conjugate compound of hyaluronic acid bonded to pentosan polysulfate, or salts or derivatives thereof, can induce chondrogenic differentiation of a population of MPCs as observed by increased, amongst other indications, glycosaminoglycan (GAG) production. The GAG expression observed for two different conjugate compounds of the invention were each significantly greater than that seen when Fps alone was present. This result is surprising as exposure of MPCs to HA alone did not produce any increase in GAG production and so the combination of HA and PPS (or a PPS derivative) in a conjugate compound could not have been predicted to produce such an increase in GAG production over PPS alone.

Definitions

In this patent specification, adjectives such as first and second, left and right, front and back, top and bottom, etc., are used solely to define one element or method step from another element or method step without necessarily requiring a specific relative position or sequence that is described by the adjectives. The terms 'comprises', 'comprising', 'includes', 'including', or similar terms are intended to mean a non-exclusive inclusion, such that a method, system or apparatus that comprises a list of elements does not include those elements solely, but may well include other elements not listed.

Unless defined otherwise, all technical and scientific terms used herein have the same meaning as would be commonly understood by those of ordinary skill in the art to which this invention belongs.

As used herein, and unless the nature of the bonding is specified, the terms "bond", "bonding" and "bonded" refer generally to an attraction or association between hyaluronic acid and pentosan polysulfate which may take the form of covalent bonding, ionic bonding, hydrogen bonding interactions or other weak electrostatic interactions.

The term "conjugate compound", as used herein, refers to a compound formed by the joining of a number of separate compounds. Particularly, the term is used herein to describe a compound formed by the joining, preferably by covalent bonding, of two separate polysaccharide molecules. Specifically, the term is used to describe a compound formed by the bonding, preferably covalent bonding, of HA and PPS or salts or derivatives of each.

As used herein, the term "derivative", particularly in relation to hyaluronic acid or pentosan polysulfate, refers to a closely related compound to the named compound in which the existing functional groups of the named compound have been modified or transformed to provide a different functionality while the core skeleton of the compound remains unchanged. Functional group modifications or transformations contemplated are those which are standard in the art. As one non-limiting example, the conjugate compound of formula (IIIa) is formed by the reaction of HA with a PPS derivative whereby the sulfate ester groups of standard PPS have been modified to present carboxylic acid groups. This carboxyl modified PPS is considered to be a derivative of PPS. References herein to HA and PPS are considered to include their salts and/or derivatives.

In certain embodiments the derivative of PPS may be selected from the group consisting of alkyl, alkenyl, carboxyl, alkanoyl, alkanoyloxy, carboalkoxy derivatives and salts such as sodium, calcium, magnesium and potassium salts thereof. The alkyl, alkenyl, carboxyl, alkanoyl, alkanoyloxy and carboalkoxy groups may be as defined hereinafter.

In certain embodiments the derivative of HA may be selected from the group consisting of alkyl, alkenyl, arylalkyl, hydroxyalkyl, aldehyde, alkanone, carboxyl, carboxamide, alkanoyl, carboalkoxy, carboaryloxy, carbonate, O-alkyl, O-aryl, O-alkenyl, O-alkanoyl and O-alkenoyl derivatives and salts such as sodium, calcium, magnesium and potassium salts thereof. The alkyl and other functional groups recited in this paragraph are as defined hereinafter.

Derivatives of the compounds or conjugate compounds described herein can be obtained by techniques known in the art. For example, hydroxy groups may be oxidised, to ketones, aldehydes or carboxylic acids by exposure to oxidising agents such as chromic acid, Jones' reagent, potassium permanganate ($KMnO_4$), peracids such as metachloroperbenzoic acid (mCPBA) or dioxiranes such as dimethyldioxirane (DMDO) and methyl(trifluoromethyl) dioxirane (TFDO). Oxidising agents may be chosen such that other functional groups in the molecule are, or are not, also oxidised. For example, a primary alcohol may be selectively oxidised to an aldehyde or carboxylic acid in the presence of secondary alcohols using reagents such as $RuCl_2(PPh_3)_3$-benzene. Secondary alcohols may be selectively oxidised to ketones in the presence of a primary alcohol using $Cl_2$-pyridine $NaBrO_3$-ceric-ammonium nitrate. Alcohols may be oxidised in the presence of double and triple bonds and without epimerisation at adjacent stereocentres using Jone's reagent. Alternatively, reagents chosen may be less selective resulting in oxidation at more than one functional group. A person skilled in the art is be able to determine suitable conditions for obtaining derivatives of isolated compounds, for example, by reference to texts relating to synthetic methodology, non-limiting examples of which are Smith M. B. and March J., March's Advanced Organic Chemistry, Fifth Edition, John Wiley & Sons Inc., 2001 and Larock R. C., Comprehensive Organic Transformations, VCH Publishers Ltd., 1989. Furthermore, selective manipulations of functional groups may require protection of other functional groups. Suitable protecting groups to prevent unwanted side reactions are provided in Green and Wuts, Protective Groups in Organic Synthesis, John Wiley & Sons inc., 3rd Edition, 1999.

As used herein, "effective amount" refers to the administration of an amount of the relevant active agent sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight, etc. An appropriate dosage or dosage regime can be ascertained through routine trial.

The term "pluripotent stem cells" or "multipotent stem cells" as used herein refers to a population of cells which can proliferate and differentiate, into a plurality of different cell lineages. Multipotent stem cells may be of adult or embryonic origin. Preferably, they are of adult origin.

In preferred embodiments the multipotent stem cells include mesenchymal precursor cells (MPCs), dental pulp stem cells (DPSCs) and periodontal ligament stem cells (PDLSCs). Both DPSCs and PDLSCs are known to be capable of differentiation into a number of cell types including chondrocytes and osteocytes. MPCs are typically undifferentiated cells that can be isolated from bone marrow and are characterized, at least partly, by the expression of cell surface markers such as STRO-1, VCAM-1 (CD106), STRO-3 (tissue nonspecific alkaline phosphatase), STRO-4 (HSP-90b) and CD146. In one embodiment, the MPCs are STRO-$1^+$ MPCs. In a particular embodiment, the MPCs are obtained or are obtainable from human bone marrow. Suitably, the STRO-$1^+$ MPCs may be selected and/or purified by antibody-mediated immunoselection. Non-limiting examples of immunoselection include flow cytometry, panning and magnetic bead selection, although without limitation thereto. The MSCs may further be derived from induced pluripotent stem cells (diPSCs) by inhibition of the TGFβ/activin signalling pathway.

The term "pharmaceutically acceptable salt", as used herein, refers to salts which are toxicologically safe for systemic or localised administration such as salts prepared from pharmaceutically acceptable non-toxic bases or acids including inorganic or organic bases and inorganic or organic acids. The pharmaceutically acceptable salts may be selected from the group including alkali and alkali earth, ammonium, aluminium, iron, amine, glucosamine, chloride, sulphate, sulphonate, bisulphate, nitrate, citrate, tartrate, bitarate, phosphate, carbonate, bicarbonate, malate, maleate, napsylate, fumarate, succinate, acetate, benzoate, terephthalate, palmoate, piperazine, pectinate and S-methyl methionine salts and the like.

The term "alkyl" refers to optionally substituted linear and branched hydrocarbon groups having 1 to 20 carbon atoms inclusive of 1 to 16 carbon atoms, 1 to 14 carbon atoms, 1 to 12 carbon atoms, 1 to 10 carbon atoms, 1 to 8 carbon atoms, 1 to 6 carbon atoms and 1 to 4 carbon atoms. Where appropriate, the alkyl group may have a specified number of carbon atoms, for example, $C_1$-$C_6$ alkyl which includes alkyl groups having 1, 2, 3, 4, 5 or 6 carbon atoms in linear or branched arrangements. Non-limiting examples of alkyl groups include methyl, ethyl, propyl, isopropyl, butyl, s- and t-butyl, pentyl, 2-methylbutyl, 3-methylbutyl, hexyl, heptyl, 2-methylpentyl, 3-methylpentyl, 4-methylpentyl, 2-ethylbutyl, 3-ethylbutyl, octyl, nonyl, decyl, undecyl, dodecyl, tridecyl, tetradecyl, pentadecyl.

The term "alkenyl" refers to optionally substituted unsaturated linear or branched hydrocarbon groups, having 2 to 20 carbon atoms, inclusive of 1 to 16 carbon atoms, 1 to 14 carbon atoms, 1 to 12 carbon atoms, 1 to 10 carbon atoms, 1 to 8 carbon atoms, 1 to 6 carbon atoms and 1 to 4 carbon atoms, and having at least one carbon-carbon double bond. Where appropriate, the alkenyl group may have a specified number of carbon atoms, for example, alkenyl which includes alkenyl groups having 2, 3, 4, 5 or 6 carbon atoms in linear or branched arrangements. Non-limiting examples of alkenyl groups include, ethenyl, propenyl, isopropenyl, butenyl, s- and t-butenyl, pentenyl, hexenyl, hept-43-diene, hex-1,3-diene, non-1,3,5-triene and the like. The term "alkenyl" embraces substituents having "cis" and "trans" orientations, or alternatively, "E" and "Z" orientations.

The term "alkanoyl" refers to an acyl moiety of a straight or branched configuration having 1 to 20 carbon atoms, inclusive of 1 to 18 carbon atoms, 1 to 14 carbon atoms, 1 to 12 carbon atoms, 1 to 10 carbon atoms, 1 to 8 carbon atoms, 1 to 6 carbon atoms and 1 to 4 carbon atoms. Examples of alkanoyl groups include, but are not limited to, acetyl, propionoyl, butyryl, isobutyryl, pentanoyl and hexanoyl.

The term "carboalkoxy" refers to an alkyl ester of a carboxylic acid, wherein alkyl has the same definition as found above. Examples include carbomethoxy, carboethoxy, carboisopropoxy and the like.

The term "alkanoyloxy" refers to an alkanoyl group linked via an oxygen bridge wherein the alkyl portion of the alkanoyl moiety may be as described above.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O. Examples of aryl groups include accordingly phenyl, naphthalenyl, tetrahydronaphthalenyl (also known as "tetralinyl"), indenyl, indanyl, anthracenyl, phenanthrenyl, benzonaptithenyl (also known as "phenalenyl"), and fluorenyl.

The definitions just provided apply to related derivatives i.e., the definitions of alkyl, alkenyl etc provided above apply to the relevant portion of O-alkyl, O-alkenyl, O-alkanoyl and other terms used herein as would be understood by a person of skill in the art.

As used herein, the terms "subject" or "individual" or "patient" may refer to any subject, particularly a vertebrate subject, and even more particularly a mammalian subject, for whom therapy or prophylaxis is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment or prophylaxis for a condition related to connective tissue degradation, particularly IVD degeneration. However, it will be understood that the aforementioned terms do not imply that symptoms are necessarily present.

Conjugate Compounds and Use Thereof

Although the bulk of the following discussion addresses the use of a conjugate compound of HA-PPS to enhance the chondrogenic phenotype of MPCs it will be appreciated that the invention is not so limited. The same conjugate compounds may be employed, *mutatis mutandis*, to control of the differentiation of other multipotent stem cell types including DPSCs, PDLSCs as well as with diPSCs.

According to a first aspect of the invention, there is provided a conjugate compound comprising hyaluronic acid, or a salt or derivative thereof, bonded to pentosan polysulfate, or a salt or derivative thereof. The HA and PPS may be covalently bonded or bonded though electrostatic or other interactions, including ionic, dipole-dipole and hydrogen bonding. Whatever the bonding the HA and PPS will be strongly associated with one another to an extent substantially greater than if they were simply present in solution together. This can achieved through means including adjustment of pH, controlling the concentration of the HA and PPS to be suitably high and trapping of the PPS within a HA polymeric matrix.

Preferably, the hyaluronic add and pentosan polysulfate are covalently bonded.

Suitably, the conjugate compound is of formula HA-L-PPS wherein HA is hyaluronic acid, or a salt or derivative thereof, PPS is pentosan polysulfate, or a salt or derivative thereof, and L is a linker unit having a first reactive group reactive with a first complimentary group on hyaluronic add and further having a second reactive group reactive with a second complimentary group on pentosan polysulfate. Linker chemistry is a well developed field and a person skilled in the art of organic chemistry generally, and linker or coupling chemistry specifically, would be familiar with the available options to link HA and PPS. For example, unmodified HA presents carboxyl, alcohol and carbonyl functionalities while PPS presents carboxyl, alkoxy and sulphate ester moieties. Linker units can be chosen from a wide range available which have at least two functional groups, one to react with a HA functional group and the other to react with a PPS functional group, as both described above. Alternatively, one or more of the existing functional groups on HA and/or PPS may first undergo a functional group transformation to thereby present a more selective or reactive group for either subsequent reaction with the linker unit or direct reaction with the other of HA or PPS.

Preferably, L has a first reactive group reactive with a carbonyl or hydroxyl functional group on hyaluronic acid.

Suitably, L has a second reactive group reactive with a carboxylic acid group on pentosan polysulfate.

Preferably, the first and second reactive group are selected from the group consisting of —$NH_2$, OH and SH.

Preferably, L is a diamine. A wide range of bridging diamine linkers are commercially available such as, for example, cystamine. The diamine linker may take the form of two primary amine groups joined by a simple alkyl chain of between 1 to 20 carbon atoms, inclusive of 1 to 16 carbon atoms, 1 to 14 carbon atoms, 1 to 12 carbon atoms, 1 to 10 carbon atoms, 1 to 8 carbon atoms, 1 to 6 carbon atoms and 1 to 4 carbon atoms. Alternatively, the chain may be branched and/or one of the amine groups may be presented from a branch of the main chain or the chain may present double or triple bonds. Further, the diamine linker may have a chain comprising one or more heteroatoms. The heteroatoms may be part of functionalities such as disulphide, thioether, ether, amide and others common in the art.

In certain embodiments the HA may also present a further functionality suitable for cross linking to incorporate the HA, and bound PPS, into a hydrogel. The further functional group may be a hydroxyl group including a phenolic or benzyl hydroxyl group.

In one embodiment, the conjugate compound of the first aspect is a conjugate compound of formula (I), or a salt thereof:

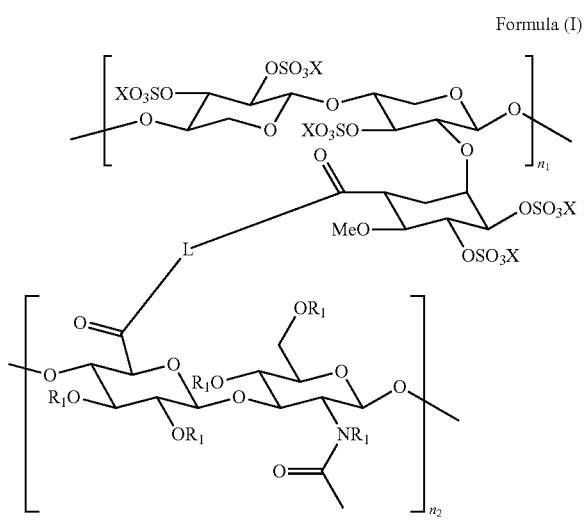

Formula (I)

wherein, $n_1$ is sufficient to provide a molecular weight of between 1,000 to 20,000 daltons for the pentosan polysulfate component of the conjugate and $n_2$ is sufficient to provide a molecular weight of between 5,000 to 20,000,000 daltons for the hyaluronic acid component of the conjugate.

each X is independently a salt forming ion selected from the group consisting of sodium, calcium, magnesium and potassium ions OR X may be selected from hydrogen, alkyl, alkenyl, carboxyl, alkanoyl, alkanoyloxy and carboalkoxy;

each $R_1$ group is independently selected from a salt forming ion, hydrogen, alkyl, alkenyl, arylalkyl, hydroxyalkyl, aldehyde, alkanone, carboxyl, carboxamide, alkanoyl, carboalkoxy, carboaryloxy, carbonate, O-alkyl, O-aryl, O-alkenyl, O-alkanoyl and O-alkenoyl; and L is a linker unit as previously described.

Preferably, $n_1$ is sufficient to provide a molecular weight of between 2000 to 10,000 daltons, more preferably 4000 daltons to 8000 daltons, most preferably between 5000 daltons to 6000 daltons for the pentosan polysulfate component of the conjugate.

Preferably, $n_2$ is sufficient to provide a molecular weight of between 50,000 daltons to 2,000,000 daltons, more preferably between 100,000 daltons to 500,000 daltons, most preferably between 200,000 daltons to 250,000 daltons for the hyaluronic acid component of the conjugate.

In one embodiment L is $R_2$ which is selected from alkyl, aminoalkyl, diaminoalkyl, acyl, aryl, ether each of which may contain one or more further heteroatoms selected from sulphur, oxygen and nitrogen The conjugate compound of formula (I) represents a covalently bonded conjugate of PPS, or a derivative thereof, represented by the structure within the bracket defined by $n_1$, and HA, or a derivative thereof, as represented by the structure within the bracket defined by $n_2$. The skilled addressee will appreciate that the exact value of $n_1$ and $n_2$ will vary based on the particular PPS and HA starting materials chosen. The molecular weight of the pentosan polysulfate may differ between different manufacturers and, to some extent, even between different batches from the same manufacturer. Further, there is a wide range of commercially available HA products of different molecular weight. It will also be appreciated that, in any event, the n values are simply weighted averages of the natural variation in molecular weights observed for such polysaccharide products.

Further, PPS is a polysaccharide composed of repeating units of 1-4 linked beta-D-xylopyranose with substituted 4-methylglucopyranosyluronic acid units being presented, on average, every tenth xylopyranose unit. It will therefore be understood that the structure shown in the formulae described herein, and the n values associated therewith, takes into account that the 4-methylglucopyranosyluronic acid is only present every tenth xylopyransose repeat unit although, for the sake of brevity, this has not been explicitly indicated in the structures shown.

Further still, it will be understood that not every available carboxyl group of the HA or PPS will be involved in binding. Both HA and PPS are polymeric structures with relatively high molecular weights and so when they are functionalised or bound together it is expected that only a portion of those available groups will actually participate in the reaction. The above points would be evident to a person of skill in the art upon reviewing the structures herein and would appreciate that they are best representations of the actual chemistry occurring.

In one preferred embodiment the corrugate compound of formula (I), is a conjugate compound of formula (II), or a salt thereof:

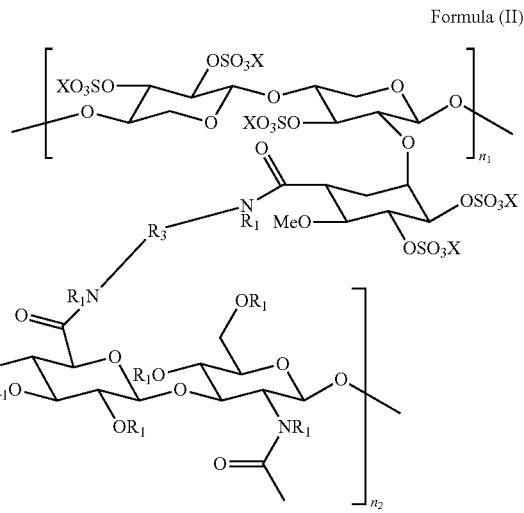

Formula (II)

wherein X, $R_1$, $n_1$ and $n_2$ are as already described and wherein, $R_3$ is selected from alkyl, disulphide, alkyldisulphide, acyl, ether, carboalkoxy and alkanoyloxy.

The HA component may present a further functional group at carboxyl groups not involved in PPS binding, as discussed above. These will take part in cross linking reactions with a further polymeric structure to incorporate the conjugate compound into a hydrogel.

In one highly preferred embodiment the conjugate compound of formula (I) is a conjugate compound of formula (III), or a salt thereof:

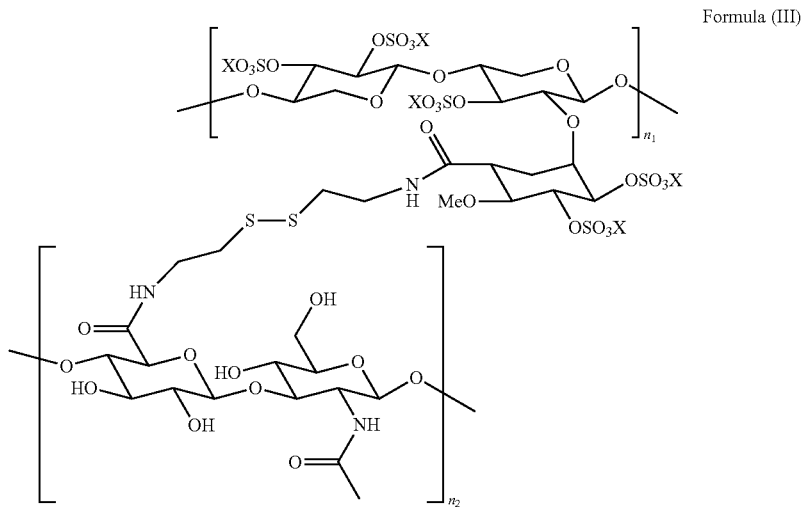

Formula (III)

wherein $n_1$ and $n_2$ and X are as already described.

Preferably, X is sodium. The conjugate compound of formula (III) represents the conjugation of PPS, of which different salt forms are commercially available, with HA in their unmodified form. References herein to the experimental use of HA-PPS can be taken as reference to a conjugate compound of formula (III) wherein X is sodium. As described above, unbound carboxyl groups of the HA may present a further functionality for hydrogel incorporation.

In a further highly preferred embodiment the conjugate compound of formula (I) is a conjugate compound of formula (IIIa), or a salt thereof:

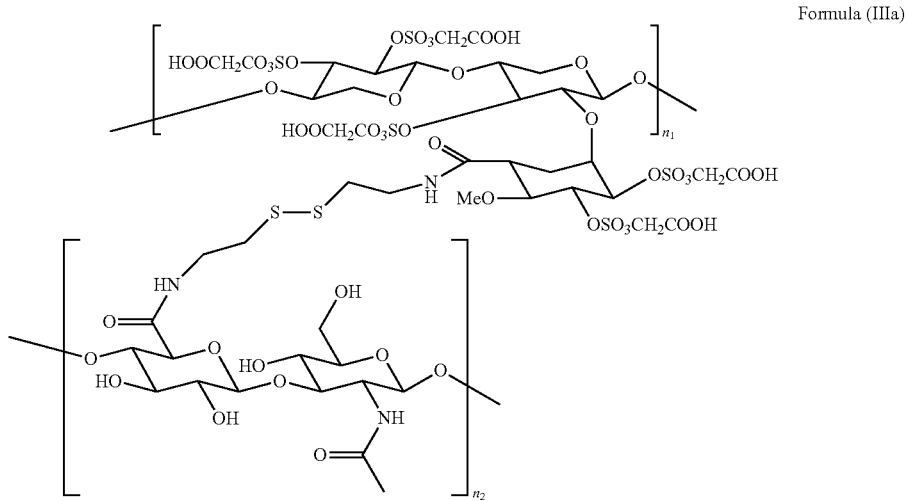

Formula (IIIa)

wherein $n_1$ and $n_2$ are as defined above.

The conjugate compound of formula (IIIa) represents the conjugation of a modified PPS with HA in its unmodified form. Specifically, the PPS has been modified to present carboxyl groups by reaction at its sulphate ester moieties. This carboxyl modified PPS will be referred to herein as $PPS_{COOH}$ and the conjugate compound of formula (IIIa) can be specifically referred to as HA-$PPS_{COOH}$. As described above, unbound carboxyl groups of the HA may present a further functionality for hydrogel incorporation.

According to a second aspect of the invention there is provided a method of synthesising a conjugate compound of the first aspect including the step of coupling hyaluronic acid, or a derivative thereof, to pentosan polysulfate, or a derivative thereof, via a covalent bond.

Preferably, the hyaluronic acid and/or pentosan polysulphate, or a salt or derivative thereof, are first chemically modified, as discussed above, to present a linker unit prior to covalent bonding.

Suitably, the hyaluronic acid, or salt or derivative thereof, is chemically modified to present a linker group having a primary amine functionality.

Preferably, the chemical modification of the hyaluronic acid, or salt or derivative thereof, is performed via a carboxyl group activation pathway using a carboxyl activating group. Preferably, the carboxyl activating group is an imide, more preferably it is a carbodiimide such as 1-ethyl-3-(3-dimethylaminopropyl) carbodiimide (EDC), and/or a succinimide such as N-hydroxysuccinimide ester.

Suitably, the primary amine of the hyaluronic acid linker group is reacted with a carboxyl group on the pentosan polysulfate, or salt or derivative thereof.

Figure 2:
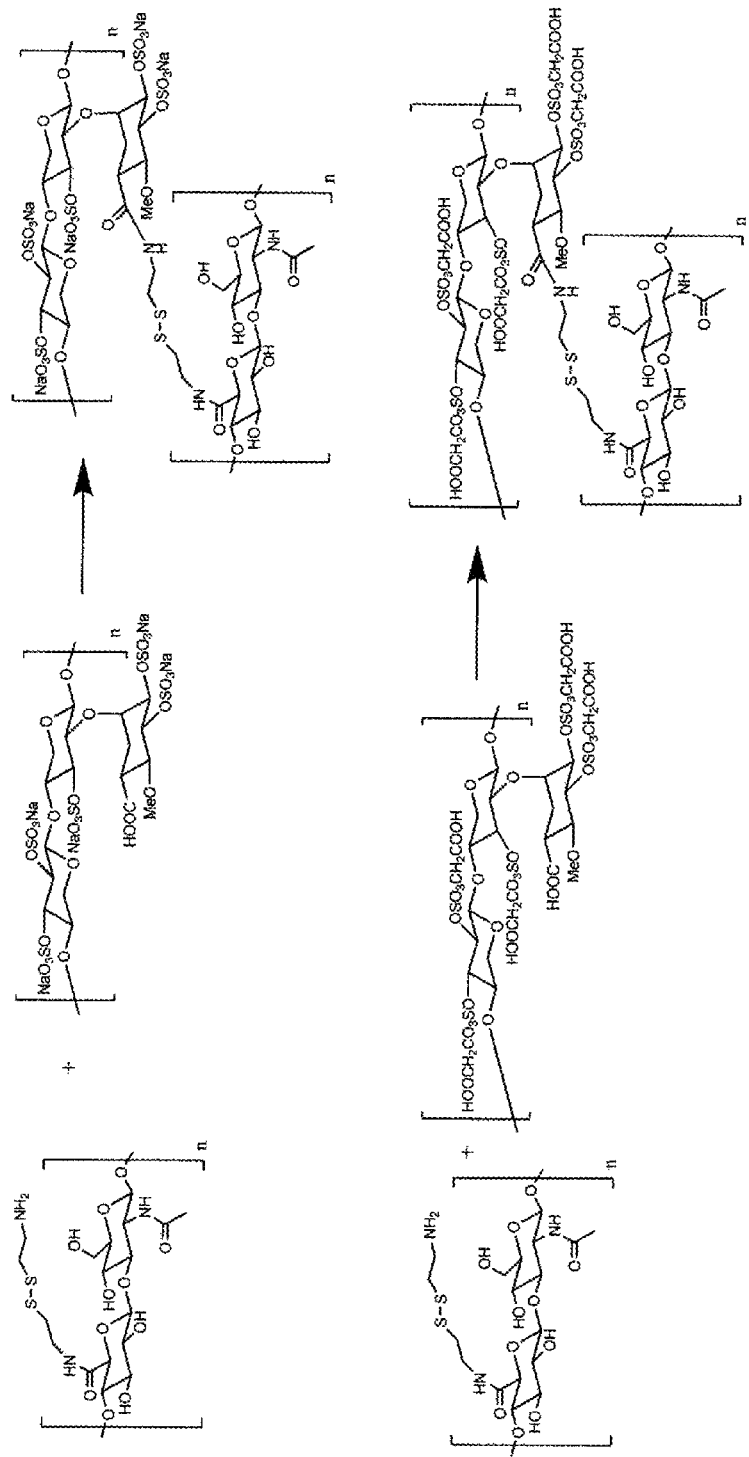
FIG. 2 shows reaction schemes representing the synthesis of HA-PPS and HA-PPS$_{COOH}$ using the functionalised HA of FIG. 1.

By way of example, one possible synthetic pathway to provide a conjugate compound of the present invention is described in FIGS. 1 and 2. FIG. 1 is a reaction scheme for the functionalisation of HA to present a linker unit while FIG. 2 shows reaction schemes representing the synthesis of HA-PPS (i.e. an unmodified PPS bound to HA) and HA-PPS$_{COOH}$ using the functionalised HA. These reactions are discussed in detail in the experimental section but, in general terms, the HA functionalisation step involves the coupling of the diamine linker unit to the free carboxyl of the glucuronic acid sugar of HA. The coupling is performed using standard EDG/NHS coupling chemistry. The modified HA is then coupled to PPS$_{Na}$ and PPS$_{COOH}$ to provide the conjugate compound products. The scheme of FIG. 2 shows that the coupling occurs at the carboxyl group of the 4-methylglucopyranosyluronic acid of the PPS or PPS$_{COOH}$. Thus, a HA will be coupled to every tenth xylopyranose repeat unit of PPS. This coupling step is also performed using standard EDC/NHS coupling chemistry. The characterisation of the functionalised HA and the HA-PPS and HA-PPS$_{COOH}$ conjugates is presented in the experimental section and accompanying figures.

It should be noted that prior to the diamine functionalisation of HA it may be reacted with a compound which can assist with the later cross linking step to form a hydrogel, if such an approach is desired. In one embodiment, the HA will be reacted with a compound which presents both an amine group for reaction at a portion of the HA free carboxyl groups, and a hydroxyl group for later reaction with a functional group presented by PEG to allow cross linking and so hydrogel formation. One preferred example of such a compound is a tyramine salt. Thus the HA will initially be functionalised, to an extent, with tyramine to present a phenolic hydroxyl group before subsequently undergoing reaction with the diamine linker, as described, to thereby present a functionalised HA species ready to be coupled with PPS or PPS$_{COOH}$ and to subsequently undergo a radical coupling reaction with functionalised PEG. In the experimental section the tyramine functionalised HA is referred to as HA-$_{TYR}$ and when this compound is subsequently further functionalised with the diamine linker it may be referred to as HA-$_{TYR}$-NH$_2$.

A third aspect of the invention resides in a conjugate compound produced by the method of second aspect. The conjugate compound is a hyaluronic acid/PPS conjugate as described for the first aspect of the invention.

According to a fourth aspect of the invention there is provided a pharmaceutical composition comprising an effective amount of a conjugate compound of the first or third aspect, or a pharmaceutically acceptable salt thereof, and a pharmaceutically acceptable carrier, diluent and/or excipient.

A fifth aspect of the invention resides in a method of treating or preventing a disease, disorder or condition responsive to connective tissue repair and/or maintenance in a patient including the step of administering an effective amount of a conjugate compound of the first or third aspect and pluripotent or multipotent stem coils, and/or progeny cells thereof, or the pharmaceutical composition of the fourth aspect to the affected or potentially affected tissue.

A sixth aspect of the invention provides for a conjugate compound of the first or third aspect, or a pharmaceutically acceptable salt thereof, for use in the treatment or prophylaxis of a disease, disorder or condition responsive to connective tissue repair and/or maintenance in a patient.

A seventh aspect of the invention resides in a method of enhancing, promoting or maintaining the chondrogenic potential of a stem cell including the step of contacting the stem cell with the conjugate compound of the first or third aspect.

An eighth aspect of the invention resides in a method of reducing or inhibiting the osteogenic differentiation of a stem cell including the step of contacting the stem cell with the conjugate compound of the first or third aspect. The stem cell may be selected from the group consisting of MPCs, DPSCs and PDLSCs.

A ninth aspect of the invention resides in the use of the conjugate compound of the first or third aspects in the manufacture of a medicament for the treatment or prophylaxis of a disease, disorder or condition responsive to connective tissue repair and/or maintenance.

Suitably, the pharmaceutical composition is for the treatment or prophylaxis of a disease, disorder or condition responsive to connective tissue repair and/or maintenance, such as connective tissue degeneration.

In one embodiment, the pharmaceutical composition further comprises multipotent stem cells. In one particular embodiment, the pharmaceutical composition may take the form of a polymeric matrix within which the conjugate, compound of the first or third aspect and a multipotent stem cell population are located. Preferably, the polymeric matrix is a hydrogel. Suitably, the hydrogel is comprised of cross linked polyethylene glycol and hyaluronic acid units. This pharmaceutical composition is suitable for use with the methods of the invention. The chondrogenic or osteogenic differentiation of the multipotent stem cells may be promoted.

The hydrogel may be formed by cross linking of tyramine functionalised HA and PEG functionalised with a hydroxy-acid such as 3-(4-hydroxyphenyl)propionic acid (HPA). Further functionalities suitable for achieving cross linking to effect hydrogel formation may be suitable and would be well known in the art of polymer chemistry. The conjugate compounds of the invention may, in one embodiment, be present during the cross linking initiation step such that they become incorporated, i.e. bound, into the hydrogel scaffold. This is a particularly preferred embodiment for treatment of IVD degeneration due to the physical structure of the functionalised hydrogel which may be injected into the site of damage.

The MPCs can also be present at hydrogel formation to thereby have them effectively encapsulated into the hydrogel matrix and in contact with bound conjugate compounds of the invention.

The pharmaceutical composition may comprise further additives selected from the group consisting of glycosaminoglycan (GAG), unbound hyaluronic acid (HA), chondroitin sulphate, dermatan sulphate, keratin sulphate, heparin, heparin sulphate and unbound PPS. These additives may bring additional benefit to MPC differentiation or may contribute more directly to repair of connective tissue.

The pharmaceutical composition may include more than one conjugate compound of the first or third aspect. When the composition includes more than one conjugate compound then the conjugate compounds may be in any ratio. Preferably, the conjugate compound of the first or third aspect in the pharmaceutical composition is HA-PPS and/or HA-PPS$_{COOH}$.

The conjugate compounds of the first or third aspect are present in the pharmaceutical composition in an amount sufficient to prevent, inhibit or ameliorate the disease, disorder or condition which is the subject of treatment. Suitable dosage forms and rates of the compounds of the first or third aspect and the pharmaceutical compositions containing such may be readily determined by those skilled in the art.

Dosage forms may include tablets, dispersions, suspensions, injections, solutions, syrups, troches, capsules and the like. These dosage forms may also include injecting or implanting devices designed specifically for, or modified to, ensure placement at the site of connective tissue degradation. A hydrogel is a preferred delivery form.

The disease, disorder or condition to be treated will be caused by or in some way related to connective tissue degradation and will be responsive to connective tissue repair and/or maintenance and/or reconstitution.

Preferably, the affected tissue is a cartilaginous structure, such as an intervertebral disc, articular cartilage or a meniscus; bone; tendon; ligament; and components of teeth.

The conjugate compound of the first or third aspects and multipotent stem cells, and/or progeny cells thereof, may be co-administered. Preferably, the conjugate compound and multipotent stem cells, and/or progeny cells thereof, are co-administered within a polymeric matrix, such as a hydrogel.

The multipotent stem cells suitable for use with the pharmaceutical compositions and methods of the present invention may be selected from the group consisting of mesechymal precursor cells (MPCs), dental pulp stem cells (DPSCs) and periodontal ligament stem cells (PDLSCs). The multipotent stem cells may be derived from induced pluripotent stem cells (iPSCs)

Preferably, the multipotent stem cells are MPCs. According to this embodiment, the conjugate compound of the first or third aspects and the MPCs are administered to connective tissue in need of treatment under conditions which allow proliferation of the MPCs and differentiation of the MPCs into chondrocytes to thereby repair or regenerate the connective tissue. One particular example is the repair of a damaged intervertebral disc.

As used herein, "subject" or "individual" or "patient" refers to any subject for whom or which therapy is desired, and generally refers to the recipient of the therapy to be practiced according to the invention. The subject can be any vertebrate, but will preferably be a mammal. If a mammal, the subject will preferably be a human, but may also be a domestic livestock, laboratory subject or pet animal. The subject is most preferably a human adult, child or infant, who is or has been the object of treatment, observation or experiment.

Contacting multipotent stem cells with the conjugate compounds of the invention may, in one embodiment, inhibit or reduce the extent of osteogenic differentiation. It has been surprisingly found that the conjugate compounds of the invention are strongly inhibiting of osteogenic differentiation even in the presence of promoting molecules such as BMP-6. This can be useful in inhibiting the differentiation of a population of stem cells at the chondrogenic stage when they would otherwise proceed to osteogenesis. This provides an additional advantage or layer of control in treating the conditions described herein.

Although not wishing to be bound by theory, the conjugate compound of the first or third aspects induces elevated expression of chondrogenic markers including GAG, Sox9 and Collagen-II by the MPCs, which correlate with improved or enhanced chondrogenic potential. The use of these conjugate compounds in a composition, such as a hydrogel, which also contains MPCs can result in chondrogenic differentiation thereof to form a supportive cartilaginous matrix useful in the repair of degenerated cartilage-containing tissues. In the presence of osteogenic promoting factors the conjugate compound of the first or third aspects may induce elevated expression of osteogenic markers including Runx2 and Col1a1.

The following experimental section describes in more detail the formation of the conjugate compounds of the invention, their characterisation, their incorporation into a hydrogel and their effect on MPC differentiation. The intention is to illustrate the production of specific embodiments of the conjugate compound and their efficacy without limiting the invention in any way.

EXPERIMENTAL

Materials

Hyaluronic acid of 215 kDa molecular weight was purchased from Lifecore. Amine terminated 8-arm poly(ethyleneglycol) (PEG, tripentaerythritol backbone, Mw=40 kDa) was purchased from JenKem, USA. 3-(4-hydroxyphenyl) propionic acid (HPA), (N-(3-dimethylaminopropyl)-N'-ethylcarbodiimide hydrochloride (EDC), N-hydroxysuccinimide (NHS), peroxidase, Type I from horseradish (HRP, 113 U/mg solid) were all purchased from Sigma, Sodium PPS (Batch Q18) was supplied by bene-Arzheimittel GmbH (Munich, Germany). All other reagents were purchased from Gibco unless otherwise stated.

Reactions

Functionalisation of HA with tyramine to Facilitate Crosslinking

HA was reacted with tyramine hydrochloride and 1-Ethyl-3-[3-dimethylaminopropyl]carbodiimide hydrochloride/N-hydrosuccinimide (EDC/NHS) in a 1:10:0.1 molar ratio in 0.1M MES buffer, pH 4.8. Solutions of HA and tyramine were mixed to produce the desired concentration, the pH readjusted to 4.8 and EDC/NHS added. After 15 min, sodium hydroxide was used to adjust the pH to 5.8 and the reaction left to proceed for 3 hrs at room temperature with gentle agitation. Unreacted products were removed by dialysis in 3500 MWCO tubing (ThermoFisher) for 48 hrs each against 150 mM NaCl, 10% ethanol and distilled water and the purified samples freeze-dried. The product of this reaction is referred to as $HA_{TYR}$.

Functionallsation of PEG with HPA to Facilitate Crosslinking

PEG was reacted with 3-4-hydroxyphenylpropionic acid (HPA) using EDC/NHS chemistry. Briefly, HPA was dissolved in 0.1 M MES buffer to a concentration of 5 mM and the pH adjusted to 4.8. A solution of 500 µM EDC and 50 µMNHS was added and reacted for 15 min at room temperature. A solution of PEG in 0.1 M MES buffer was added to give a final concentration of 62.5 µM and the pH adjusted to 5.8. The reaction was left to proceed for 3 hrs at room temperature with gentle agitation and repeated up to four times to achieve the desired degree of functionalisation. Dialysis was performed for 24 hrs after each reaction in 150 mM NaCl solution using 3500 MWCO tubing. After the final reaction, a more extensive dialysis process of 24 hours in 150 mM NaCl, 24 hours in 20% ethanol and a further 24 hours in distilled water was performed and the samples freeze-dried.

Figure 4:
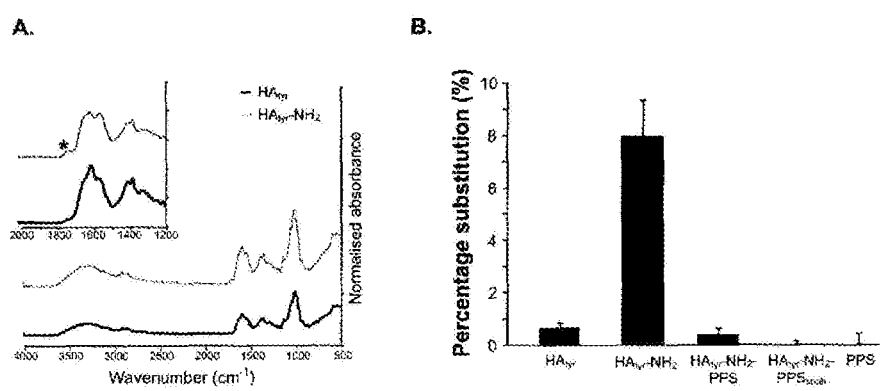
FIG. 4A is an ATR-FTIR spectrum showing the amine functionalisation of HA.
FIG. 4B is a graphical representation of the amine group content of various species.
Figure 5:
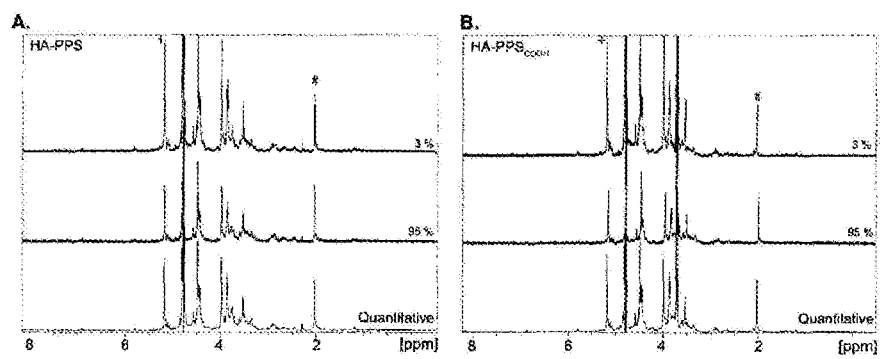
FIG. 5A is a proton NMR spectrum of HA-PPS.

Functionalisation of $HA_{TYR}$ with Amine Groups for PPS Coupling $HA_{TYR}$ was further functionalised to present amine groups using cystamine hydrochloride and EDC/NHS in a 1:10:10 molar ratio of acid groups on $HA_{TYR}$:cystamine hydrochloride:EDC. The reagents were dissolved in 0.1M MES buffer, pH 4.8 and reacted for 3 hrs at room temperature with gentle agitation. Samples were dialysed in 3500 MWCO tubing for 48 hrs each against 150 mM NaCl, 10% ethanol and distilled water prior to freeze-drying. The product of this reaction is be referred to as $HA_{TYR}$-$NH_2$ in the figures and the success of this reaction can be seen in FIG. 4 which is discussed further below.

Carboxylation of PPS

PPS was dissolved in 1M chloroacetic acid, an equal volume of 3M sodium hydroxide added and reacted at room temperature for 70 min with gentle agitation. The reaction was stopped by the addition of 4 mg/ml sodium dihydrogen phosphate and neutralised with 6N hydrochloric acid. Un-reacted products were removed by dialysis against water in 10 kDa dialysis tubing, with regular changes over a 48 hr period. The solution was freeze-dried to obtain carboxylated PPS ($PPS_{COOH}$).

Figure 3:
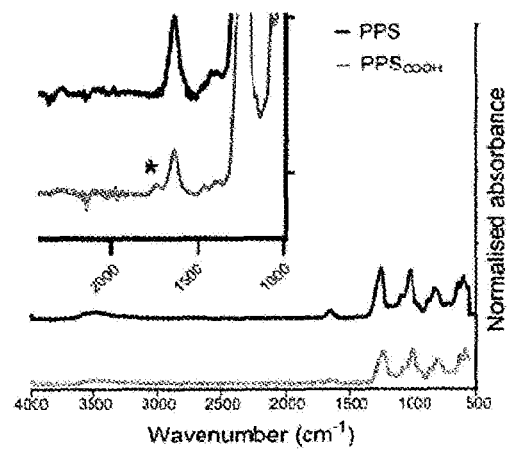
FIG. 3 is an attenuated total reflectance-Fourier transform infrared (ATR-FTIR) spectrum indicating the carboxy functionalisation of PPS.

The formation of additional carbonyl groups on the PPS following this reation can be viewed using FTIR as seen in FIG. 3. FTIR indicates the gain of a peak at 1720, corresponding to the C=O stretch from the new acid groups thereby indicating successful functionalisation.

Coupling of HA with PPS or $PPS_{COOH}$

A solution of $HA_{TYR}$-$NH_2$ and either PPS or $PPS_{COOH}$ and EDC/NHS in a 1:5:5 molar ratio was made up in 0.1M MES buffer, pH 4.8 and reacted at room temperature, with gentle agitation for 2 hrs. Samples were dialysed in 10,000 MWCO tubing for 48 hrs each against 150 mM NaCl, 10% ethanol and distilled water prior to freeze-drying. The product of this reaction is referred to in FIG. 4 as either $HA_{TYR}$-$NH_2$PPS or $HA_{TYR}$-$NH_2PPS_{COOH}$.

The success of the reaction to functionalise $HA_{TYR}$ with amine groups forming $HA_{TYR}$-$NH_2$ was confirmed by FTIR as is shown in FIG. 4A, which is an ATR-FTIR overlay of $HA_{TYR}$ and $HA_{TYR}$-$NH_2$, by the gain of a peak at 1700-1750, corresponding to the formation of an amide bond. A TNBSA assay, as seen in FIG. 4B, for amine groups also showed an increase after amine functionalisation of $HA_{TYR}$. Quantitation showed a degree of functionalisation of 8% of available acid groups in the HA molecule, providing a large number of groups available to be bound by PPS. Subsequent testing of $HA_{TYR}$-$NH_2$ after coupling with PPS or $PPS_{COOH}$ showed a decrease in the number of amine groups, suggesting that these had been removed by the coupling to PPS. NMR analysis of HA-PPS and HA-$PPS_{COOH}$ confirmed the direct coupling of PPS to HA and showed a degree of substitution of 3% for HA-PPS, with 75% of the PPS being directly bound. The degree of substitution was 8% for the HA-$PPS_{COOH}$ and gradient NMR showed that 66% of this was covalently bound to the HA.

Characterisation of Materials

TNSA Assay

The degree of amine substitution of HA was measured by 4,6-trinitrobenzene sulfonic acid (TNBSA) assay (Thermo Scientific, USA). Briefly, 100 µl of 200 µg/ml sample in carbonate buffer (2:1, vol:vol of 0.2M $Na_2CO_3$ to 0.2M $NaHCO_3$, pH 10.2) was plated out and 50 µl 0.01% TNBSA added. Samples were run in triplicate and the degree of substitution determined by comparison to a standard curve produced using glycine.

FTIR

Samples were analysed by Fourier transform infra red (ATR-FTIR) using a Thermo Scientific Nicolet 5700 spectrophotometer, equipped with an attenuated total reflectance (ATR) module (Smart Omni sampler, GE crystal). Spectra were collected in the mid-IR range (500-4000 $cm^{-1}$), at a resolution of 6.0 $cm^{-1}$ and signal averaged over 128 scans.

NMR

Quantitative 1H NMR (750 MHz) spectra were acquired on a Bruker Avance 750 high-resolution NMR spectrometer. The chemical shifts were referenced to the solvent resonance ($D_2O$) at $\delta=4.77$ ppm. The degree of substitution of HPA on the PEG molecules (ds) was calculated from the relative integral of the methylene resonance from PEG ($\delta=3.7$ ppm) compared to that of the aromatic resonances attributed to the HPA ($\delta=6.8$ and 7.1 ppm), normalizing to the number of contributing protons. To ensure the peaks observed for HPA were arising from HPA covalently bound to PEG, pulsed diffusion gradient 1H NMR was employed and the variation of the aromatic peak intensities compared to the quantitative scans against the normalized methylene peak of the PEG.

Similarly, the degree of substitution of TYR on the $HA_{TYR}$ was calculated by comparing the relative peak integrals of the aromatic protons of TYR ($\delta=6.8$ and 7.1 ppm) and the HA methyl protons ($\delta=1.9$ ppm). For the HA-PPS conjugates, a comparison of the relative integrals was made between the anomeric proton of the PPS ($\delta=5.2$ ppm) and the methyl proton of HA ($\delta=1.9$ ppm) to deter the degree of PPS substitution. Pulsed gradient diffusion NMR was also performed on these samples to observe and approximate the amount of bound macromer, against the normalized HA methyl peak.

Effect of HA-PPS and HA-$PPS_{COOH}$ on MPCs in Solution

MPC Culture

Stro1-selected human MPCs were prepared by Lonza (Walkersville, USA) for Mesoblast Ltd (Melbourne, Australia) according to the isolation procedure described by Gronthos et al [7]. MPCs were cultured in alphaMEM supplemented with 100 U/ml penicillin, 100 µg/ml streptomycin (Gibco/Invitrogen Carlsbad, Calif., USA), 10% batch tested foetal bovine serum (FBS), 2 mM L-Glutamine, 1 mM Sodium Pyruvate, and 100 µM L-ascorbate-2-Phosphate. Tissue culture flasks were maintained at 37° C. in 5% $CO_2$ in an atmosphere with 95% humidity. Upon reaching 70% confluence MPCs were passaged, replating at 2000 cells/$cm^2$.

Proliferation of MPCs Treated with HA-PPS and HA-$PPS_{COOH}$

MPCs were seeded at a density of 2000 cells/cm2 in a 96-well plate and allowed to adhere for 4 hrs at which point the medium was exchanged for MPC maintenance medium supplemented with PPS, HA, HA-PPS and HA-$PPS_{COOH}$ at concentrations equivalent to 5, 10 and 20 µg/ml unbound PPS. MPCs were cultured for 7 days with media changes every 2-3 days and the cell number determined by CCK8 assay (Sigma). Briefly, the culture medium was replaced with 100 µl MPC maintenance medium (without phenol red) containing 10% (v/v) CCX8. After 2 hrs the absorbance was read at 450 nm. All samples were performed in triplicate and normalised to blank medium without cells.

Figure 6:
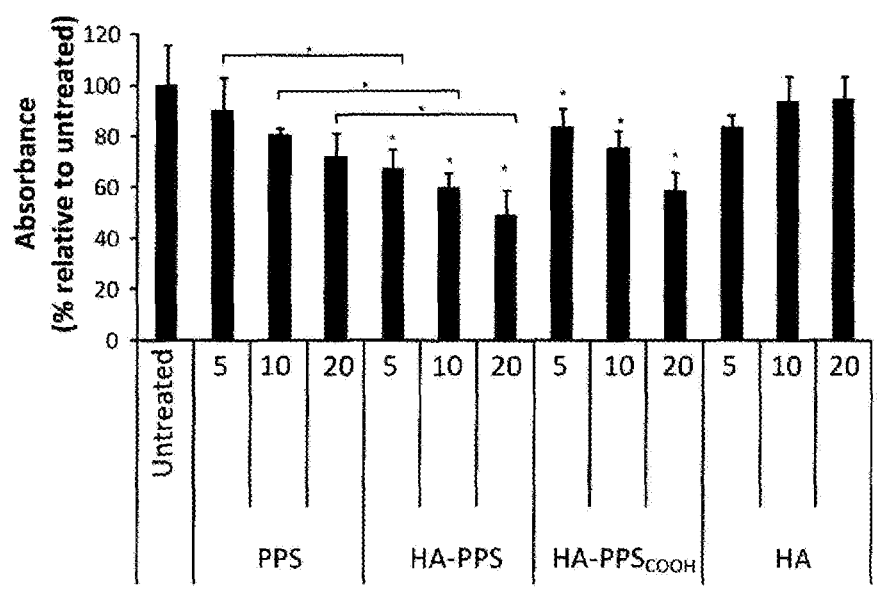
FIG. 6 is a graphical representation of the results of a CCK8 assay indicating proliferation of MPCs when treated with conjugate compounds of the invention and controls.

The effects of HA-PPS on MPC proliferation are shown in the CCK8 assay of FIG. 6 (data is shown as mean±SEM, $p<0.05$ (*), $p<0.01$ (), $p<0.001$ (*) with the results for two independent MPC donors pooled together). Treatment with both HA-PPS and HA-$PPS_{COOH}$ resulted in a dose-dependent decrease in MPC proliferation. Treatment with HA alone did not have this effect. It is likely that this corresponds with observed changes in cell morphology and induction of (chondrogenic) differentiation.

Chondrogenic Differentiation of MPCs Treated with HA-PPS and HA-$PPS_{COOH}$

Chondrogenic differentiation was compared for MPCs cultured in maintenance medium and treated with PPS, HA, HA-PPS and HA-$PPS_{COOH}$ at concentrations equivalent to 5, 10 and 20 µg/ml unbound PPS. These factors were added to the cells prior to pellet formation, which was initiated by centrifuging 2×105 MPCs in a non-adherent U-bottom plate at 500 g for 10 min. MPC pellets were cultured in 2000 medium with media changes every 3-4 days. After 21 days, samples were taken for analysis by histological staining, DMMB assay and qPCR.

Figure 7:
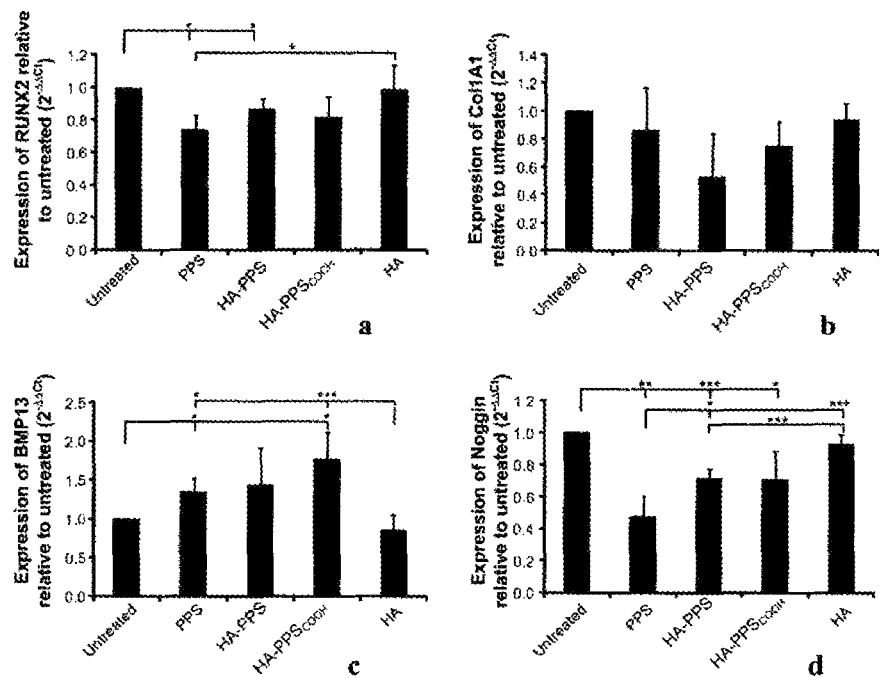
FIG. 7 is a series of graphical representations of the gene expression of MPCs which have been treated with the conjugate compounds of the invention.

The gene expression of MPCs treated with HA-PPS and HA-PPS$_{COOH}$ was analysed with the results displayed in FIG. 7 (data is shown as mean±SEM, p<0.05 (*), p<0.01 (), p<0.001 () with the results for two independent MPC donors pooled together). In the absence of any differentiation factors, both PPS and HA-PPS caused a small but significant decrease of the osteogenic transcription factor Runx2. Expression of BMP13 (which has been linked to chondrogenic differentiation) was significantly increased by PPS, HA-PPS and HA-PPS$_{COOH}$ over untreated controls. HA alone had no effect. Expression of the BMP antagonist, Noggin, was decreased by PPS treatment and to a lesser extent HA-PPS and HA-PPS$_{COOH}$. These results therefore indicate that the presence of HA-PPS and/or HA-PPS$_{COOH}$ promotes chondrogenic differentiation of MPCs.

Osteogenic Differentiation of MPCs Treated with HA-PPS

MPCs were plated at a density of 20,000 cells/cm2 and left to adhere for 24 hrs before changing the medium to osteogenic medium (DMEM-LG, 100 U/ml penicillin, 100 µg/ml streptomycin, 10% FBS, 100 ng/mL dexamethasone, 50 µM ascorbate-2-phosphate and 10 mM β-glycerophosphate) supplemented with BMP-6 (100 ng/ml) and HA-PPS at concentrations equivalent to 5, 10 and 20 µg/ml unbound PPS. Repeat experiments were also performed in the absence of FBS. The cultures were maintained for 21 days with media changes every 3-4 days. The extent of osteogenic differentiation was determined by Alizarin red staining, alkaline phosphatase staining and alkaline phosphatase activity relative to DNA content (pNPP assay).

Figure 8A:
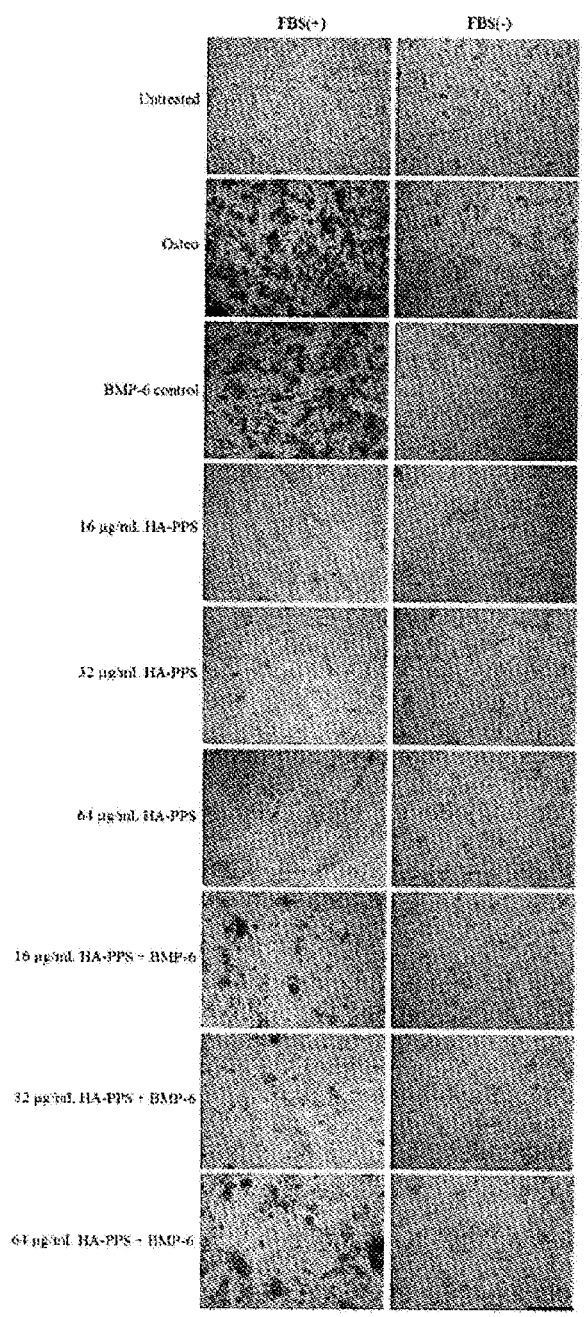
FIG. 8A is an Alizarin stain of human MSCs indicating mineralisation relative to controls in the presence of a conjugate compound of the invention and with and without addition of BMP-6.
Figure 8B:
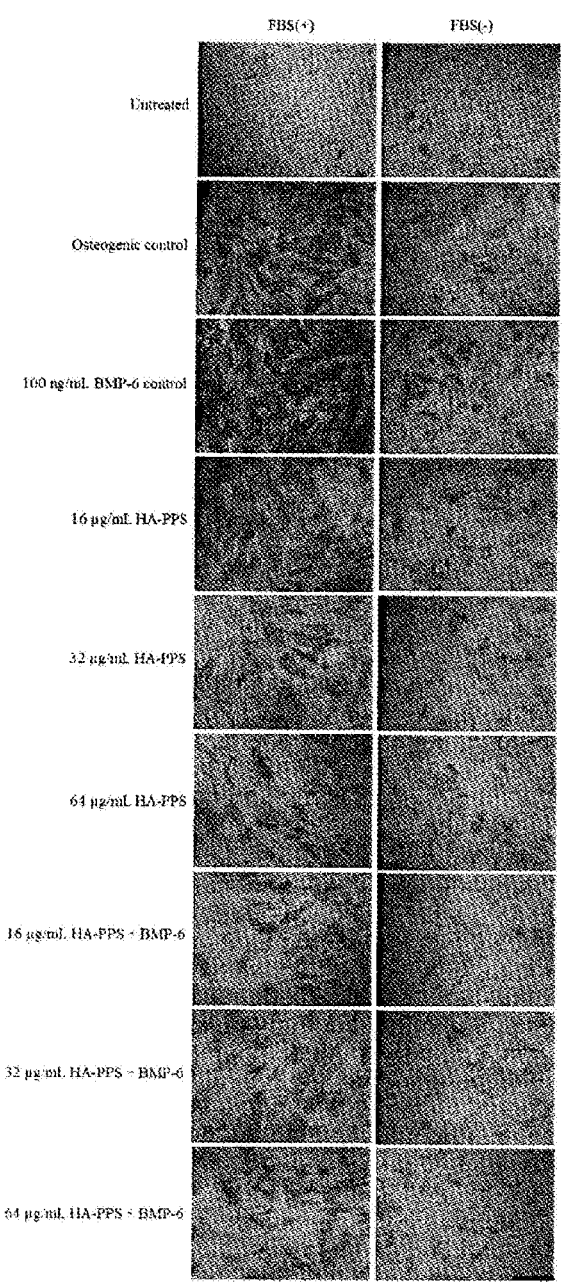
FIG. 8B is an ALP stain of human MSCs indicating alkaline phosphatise levels relative to controls in the presence of a conjugate compound of the invention and with and without addition of BMP-6.
Figure 8C:
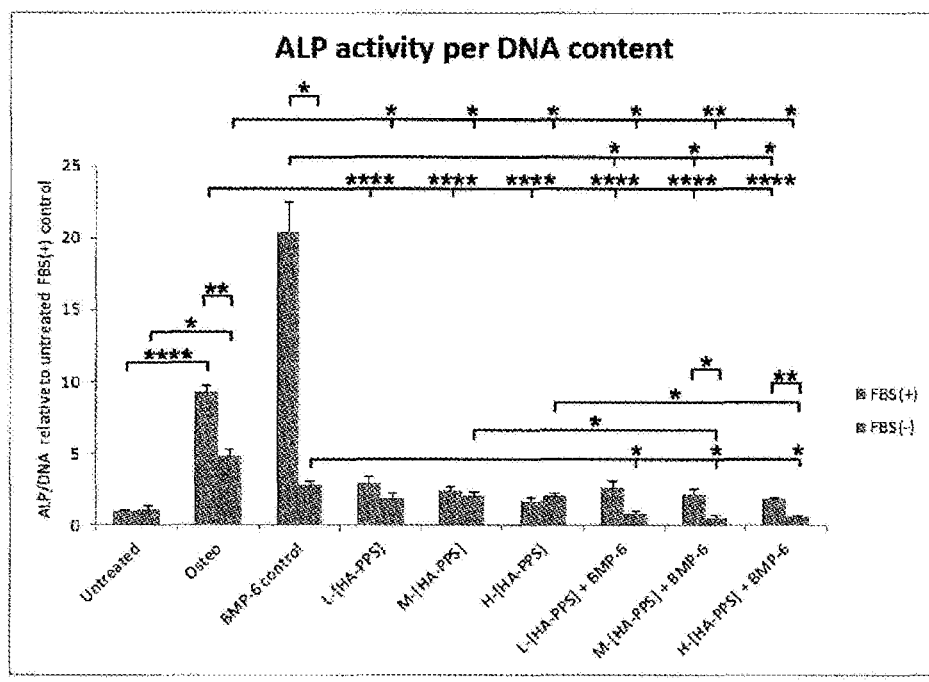
FIG. 8C is a graphical representation of the ALP activity relative to the DNA content of cells (as determined by pNPP assay)

FIGS. 8A to 8C indicate the results of this experiment. FIG. 8A is a series of images showing Alizarin red staining in FBS(+) and FBS(−) media of untreated and osteogenic controls, and at 16, 32 and 64 µg/mL HA-PPS, with and without 100 ng/mL BMP-6 at day 21 Scale bar=200 µm. The images show that there was an apparent increase in mineralization seen in the FBS(+) osteogenic and BMP-6 controls relative to the FBS(−) ones. Compared to the osteogenic control, the addition of HA-PPS at all concentrations (with or without FBS) substantially inhibits mineralisation, with similar levels as observed in the untreated control. They also show substantial reductions in mineralization having occurred in all BMP-6 conditions for the FBS(+) conditions at all concentrations of HA-PPS; these findings were not seen in the FBS(−) counterparts. Importantly, the addition of HA-PPS, at all concentrations, is seen to effectively inhibit mineralization and hence osteogenic differentiation. This is seen even when the HA-PPS was delivered along with BMP-6 with relatively low levels of mineralization observed.

FIG. 8B is a series of images showing alkaline phosphatase (ALP) staining in FBS(+) and FBS(−) media of untreated, osteogenic and BMP-6 controls, and at 16, 32 and 64 µg/mL. HA-PPS, both in the presence and absence of 100 ng/mL BMP-6 at day 7. Scale bar=200 µm. FIG. 8C shows a graphical output of the alkaline phosphatase activity relative to DNA content (pNPP assay). Reference to both of these figures demonstrates that FBS(+) media supported greater hMSC ALP activity than FBS(−) media for all conditions at day-7. All concentrations of HA-PPS in the absence of BMP-6 resulted in substantial reduction in ALP activity compared to the osteogenic control. All HA-PPS conditions with BMP-6 resulted in substantial reductions in ALP activity compared to the BMP-6 control. ALP activity did not appear to vary with change in HA-PPS concentration. Osteogenic media stained more greatly for ALP than undifferentiated media in both the presence and absence of FBS.

Alizarin Red Staining and Quantification

Day 21 osteogenic cultures were rinsed with PBS, fixed in 4% paraformaldehyde for 20 min and stained with 2% Alizarin red, pH4.2 for 30 minutes. Excess dye was removed by thorough washing with dH$_2$O and images obtained. For quantification, dye was extracted with 10% cetylpyridinium chloride in 10 mM sodium phosphate and the absorbance read at 540 nm. Samples were performed in triplicate and normalised to undifferentiated controls.

Alkaline Phosphasate (pNPP) Assay

Day 7 osteogenic cultures were lysed in 150 µl 0.1% Triton-X-100 in 0.2 M carbonate buffer and subjected to 3 freeze-thaw cycles between −80° C. and 37° C. To determine alkaline phosphatase activity, 50 µl working substrate (0.3 mg/ml pNPP (Sigma) and 3.3 mM MgCl$_2$ in 0.2 M carbonate buffer) was added to each sample and incubated at 37° C. before measurement of the absorbance on a Spectramax M5 Fluorometer (Molecular Devices) with an excitation wavelength of 405 nm. pNPP concentration was determined by extrapolation from a standard curve and normalized to both incubation time and DNA content as assessed by PicoGreen assay (Molecular Probes, performed according to the manufacturer's instructions).

DMMB Assay

Chondrogenic pellets were collected, rinsed in PBS and lysed in 1 mg/ml Papain in 100 mM sodium phosphate, 5 mM EDTA and 5 mM L-cystein (pH 6.5) overnight at 60° C. Samples of 40 µl were plated in triplicate with the addition of 10 µl 1% BSA in PBS and 50 µl 2×1,9-dimethylmethylene blue (DMMB). These were incubated at room temperature for 15 min and the absorbance at 525 nm read using a Spectramax M5 Fluorometer (Molecular Devices). Samples were normalized to DNA content as assessed by PicoGreen assay (Molecular Probes: performed according to the manufacturer's instructions).

Figure 9:
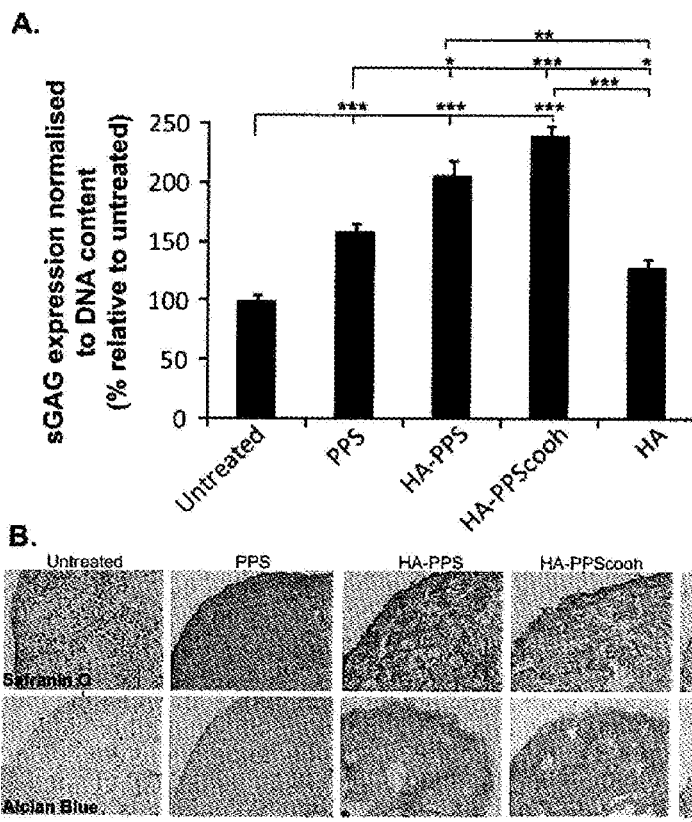
FIG. 9A is a graphical representation of the GAG expression of chondrogenic MPCs after treatment with the conjugate compounds of the invention in the absence of additional chondrogenic initiating factors.
FIG. 9B shows a series of histological sections of the chondrogenic pellet MPCs.

It is important to note that this protocol was carried out in the absence of any additional factors commonly used to initiate chondrogenesis (e.g. TGFβ). After 21 days, a DMMB assay for GAG content showed that pellets treated with PPS, HA-PPS and HA-PPS$_{COOH}$ all had significantly greater GAG content than untreated pellets or pellets treated with HA alone. These results are presented in FIGS. 9A and 9B. PPS alone increased GAG deposition to 150% of that of untreated pellets, an effect that was enhanced further with HA-PPS and HA-PPS$_{COOH}$ which had a GAG content of 200 and 250% of untreated pellets respectively, significantly higher than for PPS alone. Alcian blue and Safranin O staining (for sGAGs) also showed increased intensity for pellets treated with HA-PPS and HA-PPS$_{COOH}$ compared to unbound PPS, suggestive of a greater deposition of GAGs and proteoglycans characteristic of chondrogenic differentiation.

This is a very significant finding which demonstrates that the conjugate compounds of the invention are capable, importantly even in the absence of assisting chondrogenic factors, of strongly promoting production of important matrix materials such as GAG by MPCs due to the chondrogenic differentiation they influence. Details of the PCR analysis, sectioning and staining procedures are presented below.

Cryosectioning and Histological Staining of Chondrogenic Pellets

Samples were fixed in 4% paraformaldehyde for 20 min, rinsed with PBS and incubated m a 1:1 mixture of OCT:30% sucrose for 4 hrs followed by OCT overnight. Samples were then snap frozen and 6 µM sections taken sectioned using a Leica 3050n cryostat. Sections were stained with Alcian blue, Toluidine blue and Safranin O using standard histological procedures.

qPCR Analysis of MPC Cultures

Total RNA was extracted using an RNeasy Minikit with on-column DNase treatment (Qiagen) according to the manufacturer's instructions, cDNA was synthesized from 250 ng RNA, or the equivalent volume of DNase and RNasefree water for no-RT controls, using the SuperScript® III First-Strand Synthesis System (Invitrogen). qPCR reactions were set-up in a total volume of 10 µl with 1× Platinum SYBR Green qPCR SuperMix-UDG (Invitrogen) and 0.2 µM forward and reverse primers. A 7500 Fast Real-Time PCR System (Applied Biosystems) with fast cycling parameters of 2 min at 50° C., 2 min at 95° C. then 40 cycles of 3 sec at 95° C. and 30 sec at 60° C. followed by a melt curve was used to run the samples. Data was analysed using the $2^{-\Delta\Delta ct}$ method and normalized back to untreated monolayer levels.

HA/PEG Hydrogels Incorporating Soluble and Bound PPS
Rheological Characterisation of HA/PEG Hydrogels All rheological measurements were obtained using an AR G2 rheometer (TA Instruments, New Castle, Del.) in oscillatory mode using a 20 mm diameter stainless steel flat plate and lower Teflon Pelletier surface. The gels were synthesized and, upon addition of the $H_2O_2$, immediately vortexed and loaded between the plates of the rheometer with a gap measurement of 1000 µm. Gelation kinetics and final moduli were determined by timesweeps at 37° C., conducted with a controlled strain of 1% and an angular frequency of 6.28 rad/sec. Frequency sweeps were performed between 5.000E-3 to 50 rad/sec at 1% strain. Stress sweeps confirmed that this was within the linear viscoelastic region.

Data from the rheological characterisation of the PEG/HA hydrogels incorporating soluble PPS or HA-PPS is given in table 1. Soluble PPS was incorporated into the gel mixture prior to crosslinking, while HA-PPS was incorporated into gels to provide a covalently bound form of PPS. Rheological analysis of the properties of the resulting hydrogels showed that incorporation of both soluble and bound PPS (HA-PPS) causes a small decrease in resulting modulus and slows the gelation process, although the resulting hydrogels still maintained properties well within the limits required for transfer to clinical use.

Swelling and Degradation

To determine the degree of swelling, 50 µl gels were synthesized and the dry weight obtained after freeze-drying for 24 hrs ($W_d$). The gels were then incubated in 500 µl PBS for 24 hrs at 3° C. The PBS was removed and the gels reweighed ($W_s$). The degree of swelling was determined by $((W_s-W_d)/W_d)$ using triplicate gels for each condition. Degradation of 50 µl gels was measured over a period of 3 months using triplicate samples for each condition. After synthesis, the gels were incubated in PBS/0.01% Sodium azide at 37° C. with weekly changes of buffer. At specific tirnepoints all excess PBS was removed and the gels weighed. The degree of degradation was expressed as a % of the original gel mass.

Figure 10:
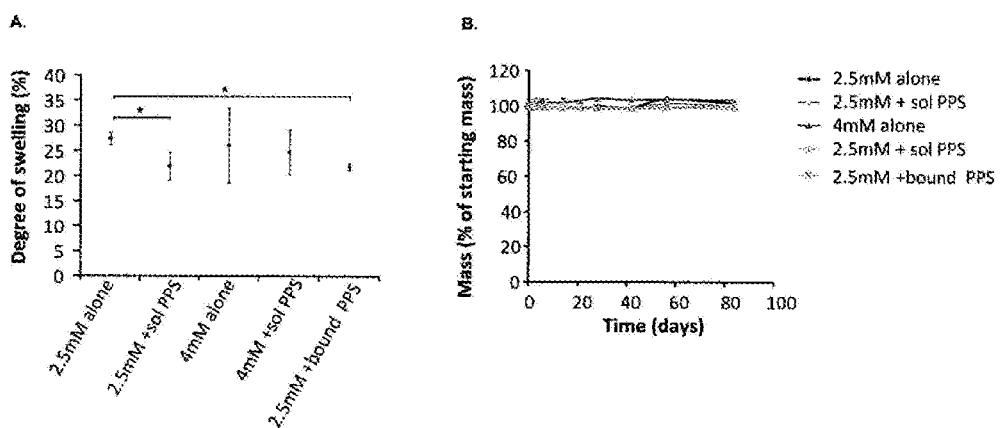
FIG. 10A is a graphical representation of the swelling profile of a HA/PEG hydrogel incorporating PPS and HA-PPS.
FIG. 10B is a graphical representation of the degradation profile of a HA/PEG hydrogel incorporating PPS and HA-PPS.

Data is presented in FIGS. 10A (swelling profile) and 10B (degradation profile) wherein all data is shown as mean±SEM, N=3, p<0.05 (*). Analysis of the swelling and degradation properties of the hydrogels showed a high degree of swelling for all hydrogels (21-27%). This was decreased (p<0.05) when PPS or HA-PPS were incorporated into the hydrogels. The degradation profile for all hydrogels were similar showing that, in the absence of cells, there was minimal degradation over a 3 month period.

The rheological, swelling and degradation data indicate that the hydrogel containing conjugate compounds of the invention have appropriate physical properties to provide an IVD scaffold which, in combination with encapsulated MPCs, results in a useful tissue engineered matrix for the treatment of IVD degeneration.

MPC Encapsulation and Culture in HA/PEG Hydrogels

MPCs (P4-6) were encapsulated in gels containing 15 mg/ml HATYR, 16.5 mg/ml PEGHPA. 0.25 U/ml horseradish peroxidase (HRP) and varying amounts of hydrogen peroxide ($H_2O_2$). Soluble PPS was added into the gels prior to crosslinking at a final concentration of 5 µg/ml. HA-PPS and HA-PPS$_{COOH}$ were incorporated at concentrations of 16 µg/ml and 9 µg/ml respectively giving a concentration of PPS equivalent to 5 µg/ml unbound PPS.

MPCs were resuspended to a concentration of $5\times10^6$ cells/ml in solution containing all of the components except $H_2O_2$ and thoroughly mixed. Crosslinking was then initiated by the addition of $H_2O_2$ and the gels spotted out into lowbinding tissue culture plates. After 15 minutes, growth media was added to the well and the cell/gel composites cultured for up to 21 days with media changes every 3-4 days.

Figure 11:
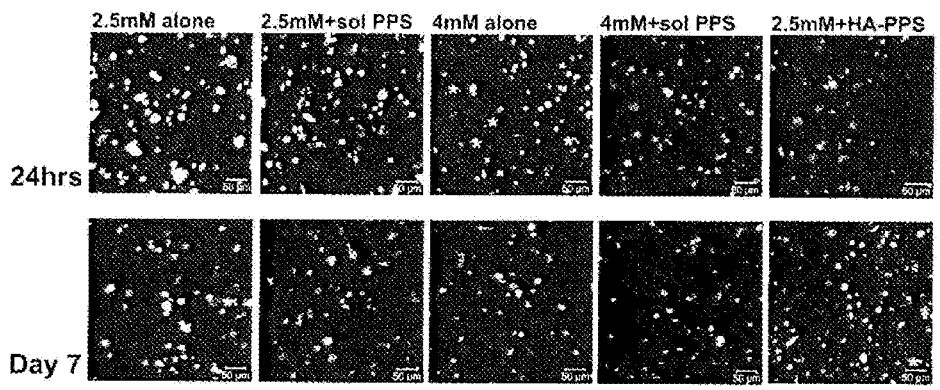
FIG. 11 is a series of images showing the viability of MPCs when encapsulated in a HA/PEG hydrogel incorporating PPS and HA-PPS.
Figure 12:
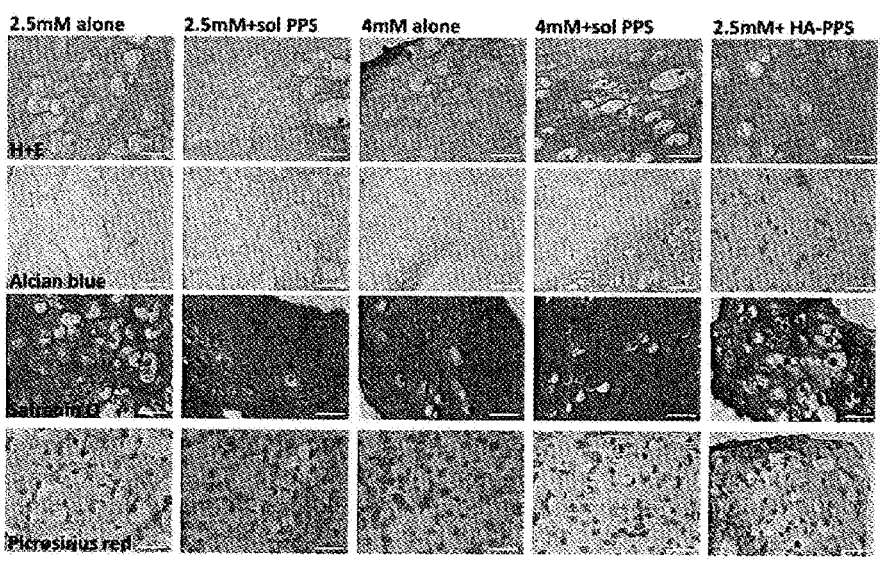
FIG. 12 is a series of histological stains indicating the structure and composition of MPC/hydrogel composites.

When encapsulated in HA/PEG hydrogels containing PPS and HA-PPS, MPCs retained good viability both after the initial cross-linking process and for longer term culture periods as shown in FIG. 11 which is a live/dead staining of encapsulated MPCs. Viability of MPCs after 24 hrs and 7 days of encapsulation is shown with live cells in green and dead cells in red (white stars). Scale bar=50 µm. The images indicate the vast majority of cells remain live Histological staining was also used to analyse the structure and matrix content of MPC/hydrogel composites after 21 days culture and the results are shown in FIG. 12. H+E staining shows gels embedded within lacunae with a structure analogous to that of native cartilage tissue. Alcian blue staining was enhanced in gels incorporating HA-PPS, with strong staining particularly evident directly around the encapsulated MPCs. This suggests increased GAG accumulation surrounding MPCs in gels incorporating HA-PPS, as compared to blank gels or those incorporating soluble PPS. Once again, the chondrogenic differentiation of the MPCs when exposed to a conjugate compound of the invention is shown and this time when within the hydrogel matrix.

Immunofluorescence

Samples were fixed in 4% paraformaldehyde for 20 min and rinsed with PBS. To detect Collagen-II, the samples were digested with 0.01% pepsin (w/v) in 0.01M HCL (pH2) for 30 min at 37° C. and incubated in 0.1% Triton-X-100 for 5 mm at RT° C. before blocking in 2% BSA/2% goat serum for 1 hr. A Collagen-II antibody (Abram ab3092) was used at a dilution of 1/50 for 2 hrs followed by incubation with an AlexFluor 488-conjugated secondary antibody for 1 hr. All samples were counterstained with Hoechst 33342, mounted in Vectorshield (Vector laboratories) and imaged by taking z-stacks through the gel with LSR710 confocal microscope (Zeiss).

Figure 13:
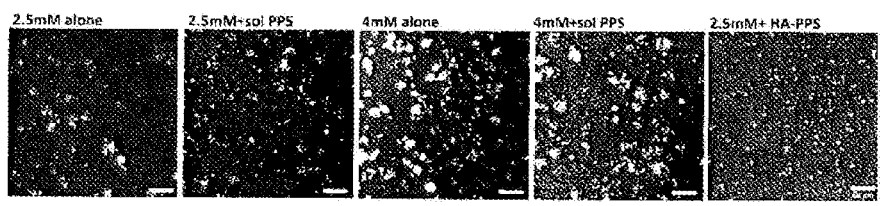
FIG. 13 is a series of stains of MPC/hydrogel composites for collagen-II deposition.

The staining procedure showed deposition of collagen-II around the encapsulated MPCs which was increased in the presence of PPS and HA-PPS compared to gels alone, as seen in FIG. 13. It was also enhanced in soft gels (cross-linked with 4 mM $H_2O_2$) compared to stiff (2.5 mM) gels.

qPCR of MPCs Encapsulated in HA/PEG Hydrogels

Figure 14:
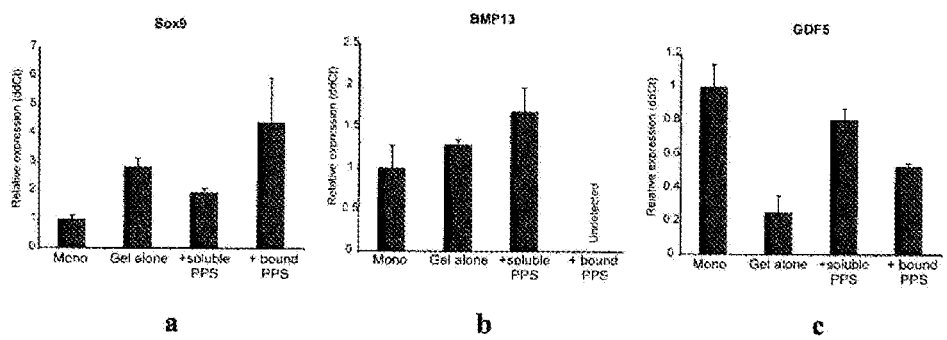
FIG. 14 is a series of graphical representations indicating the expression of various factors by IPCs encapsulated within a HA/PEG hydrogel incorporating HA-PPS.

Total RNA was extracted with QIAzol, DNase treated in suspension for 40 min at room temperature and subsequently repurified by QIAzol extraction. cDNA was synthesized from 50 ng RNA, or the equivalent volume of DNase and RNase-free water for no-RT controls, using the SuperScript® III First-Strand Synthesis System (Invitrogen). qPCR reactions were set-up in a total volume of 10 µl with 1× Platinum SYSR Green qPCR SuperMix-UDG (Invitrogen) and 0.2 µM forward and reverse primers. A 7500 Fast Real-Time PCP System (Applied Biosystems) with fast cycling parameters of 2 min at 50° C., 2 min at 95° C. then 40 cycles of 3 sec at 95° C. and 30 sec at 60° C. followed by a melt curve was used to run the samples. Data was analysed using the $2^{-\Delta\Delta ct}$ method and normalized back to untreated monolayer levels.

qPCR analysis of MPCs encapsulated for 21 days showed increased expression of the chondrogenic transcription factor, Sox9, in gels incorporating HA-PPS as seen in FIG. 14 (data is shown as mean±SEM, N=3). Once again the hydrogel incorporating a conjugate compound of the invention and MPCs is shown to have potential as a treatment for conditions responsive to connective tissue repair or reconstitution and, particularly, for those conditions where placement of a physical scaffold is useful such as in treating IVD degeneration.

Further Experiments Using Canine Mesenchymal Stem Cells (MSCs) from Induced Pluripotent Stem Cells (diPSCs)

Chen and colleagues [9] have described a methodology whereby human induced pluripotent stem cells (iPSCs) and embryonic stem cells (ESCs) could be induced to differentiate into MSCs via inhibition of the TGFβ/activin signaling pathway and maintenance in culture conditions that support an epithelial to mesenchymal transition. By exposing the cells to the TGFβ/activin type I receptor inhibitor SB431542 for just 10 days, and then transitioning the cells into typical MSC culture conditions, Chen and co-workers generated iPSC- and ESC-derived MSCs that resembled primary MSCs in terms of their immunophenotype and in their ability to differentiate into mesodermal derivatives.

This SB431542 induction method, initially described for human pluripotent stem cells, was applied herein to canine iPSCs. Using this methodology canine iPSC-derived MSCs were produced that have an immunophenotype similar to tissue-derived canine MSCs, a high proliferative rate which does not diminish with progressive passage and an ability to give rise to the three mesoderm derivatives of cartilage, bone and adipose tissue, but which do not form teratomas. The behaviour of the canine iPSC-derived MSCs when incorporated into injectable hydrogel scaffolds designed to optimise chondrogenesis within the milieu of a joint was examined.

Generation and Maintenance of diPSCs-Derived MSCs

Canine iPSCs (diPSCs) were cultured by known means and were induced to undergo an epithelial to mesenchymal transition using the protocol described by Chen [9]. Colonies of diPSCs were enzymatically passaged with TrypLE (Life Technologies) to yield large clumps of cells which were then plated onto T25 tissue culture flasks (Costar) coated with Matrigel (BD Biosciences). Cells were cultured for 10 days with 10 MM of the TGFβ/activin type I receptor inhibitor SB431542 (Stemgent) in the medium previously used to support the diPSCs (Knockout DMEM (Life Technologies), 20% (v/v) Knockout Serum Replacement (KSR) (Life Technologies), 0.1 mM non-essential amino acids (NEAA) (Life Technologies) and 2 mM L-glutamine (Life Technologies)) but without β-mercaptoethanol and leukaemia inhibitory factor. After 10 days, cells were passaged with TrypLE to yield a single-cell suspension and plated directly onto T75 tissue culture flasks (Costar). From this point cells were cultured in MSC medium consisting of Knockout DMEM (Life Technologies), 10% (v/v) ESC-qualified fetal bovine serum (Life Technologies), 0.1 mM NEM and 2 mM L-glutamine. All cultures were maintained at 37° C. with 5% $CO_2$. Commercially available canine adipose-derived adult MSCs were kindly supplied by Regeneus Pty Ltd. Vials were thawed and plated onto tissue culture flasks and maintained in MSC medium as described for the diPSC-derived MSCs.

During 10 days of culture with SB431542 it was observed that the diPSCs became organised into a monolayer and assumed a cuboidal to stellate appearance, with cells becoming more stellate rather than cuboidal at the periphery of the colony. After passage into MSC medium, and plating onto uncoated plastic, stellate-shaped cells were uniformly distributed as single cells, rather than an epithelial-like sheet, and closely resembled adipose-derived primary adult MSCs. DiPSC-MSCs express the typical MSC surface markers CD73, CD90 and CD105 as do the adult adipose-derived MSCs and the diPSCs. In contrast, expression of the MSC marker STRO1 has been acquired by the diPSC-MSCs since it is not expressed by the diPSCs. Flow cytometry confirmed that the majority of the diPSC-MSCs are positive for the cell surface markers CD73, CD90, CD105 and STRO1, DiPSC-MSCs, and adult canine MSCs, also express the pluripotency factors OCT4, NANOG and REX1. Expression of cOCT4 and cNANOG were confirmed at the transcriptional level for both the diPSC-MSCs and adult MSCs, with the diPSCs serving as a positive control.

In Vitro Osteogenic, Chondrogenic and Adipogenic Differentiation Assays

The ability of the diPSC-MSCs to differentiate into mesodermal derivatives was successfully demonstrated using the Stem-Pro Osteogenesis, Chondrogenesis and Adipogenesis Differentiation Kits (Life Technologies), according to the manufacturer's instructions. To assess for osteogenesis and chondrogenesis, cultures were stained with Alizarin Red S and Alcian Blue (pH 1.0), respectively, as per standard protocols. Adipogenesis was determined by staining with HCS LipidTOX Red (Life Technologies) according to the manufacturer's instructions. Nuclei were visualised with DAPI.

Encapsulation and Culture of diPSC-MSCs in Hydrogels

Hydrogels were prepared as described earlier. Hydrogels of 3 different compositions were used a) polyethylene glycol (PEG) (JenKem); b) PEG and hyaluronic acid (HA) (Lifecore) and c) PEG, HA and HA-pentosan polysulphate (PPS) (HA conjugated to pentosan polysulphate prepared as described hereinbefore). DiPSC-MSCs were encapsulated in the hydrogels at a density of 1×10⁷ cells/ml, 50 µl of cell/hydrogel composite was spotted onto glass coverslips and placed into 48-well low binding tissue culture plates (Costar). Triplicates of each of the 3 types of hydrogel were cultured in each of 3 types of medium: basal medium (DMEM supplemented with 100 U/ml penicillin, 100 µg/ml streptomycin and 10% fetal bovine serum (FBS) (all Life Technologies)); osteogenic medium (DMEM supplemented with 100 U/ml penicillin, 100 µg/ml streptomycin, 10% FBS, 100 ng/mL dexamethasone (Sigma), 50 µM ascorbate-2-phosphate (Sigma) and 10 mM β-glycerophosphate (Sigma)) and chondrogenic medium (DMEM high glucose supplemented with 100 U/ml penicillin, 100 µg/ml streptomycin, 10 mg/mL insulin (Life Technologies), 5.5 mg/mL transferrin (Life Technologies), 5 ng/mL sodium selenite (Life Technologies), 3 mM linoleic acid (Life Technologies), 3 mM oleic acid (Life Technologies), 1 mg/mL BSA (Life Technologies). 10 ug/ml sodium pyruvate (Life Technologies), 4 mg/ml L-proline (Sigma), 1 mM dexamethasone, 50 µM ascorbate-2-phosphate and 10 µg/ml TGFβ3 (Peprotech)). Cell/hydrogel composites were cultured for 21 days, with medium changes every 3 days, before processing for histology. Paraffin sections were stained with haematoxylin and eosin, Alizarin red S and Alcian blue (pH 2.0) according to standard protocols.

After encapsulation in the hydrogel matrix, diPSC-MSC/hydrogel composites were spotted onto glass coverslips in tissue culture plates. Under these three-dimensional conditions the cells adopted a rounded morphology that was maintained for the 21-day culture period. The structure of the cell/hydrogel composites was assessed by haematoxylin and eosin staining after 21 days and showed a relatively even distribution of cells throughout all of the hydrogel matrices with the rounded cells residing within lacuna-like structures. Interestingly, the size of these lacunae was much larger in the gels containing PEG alone than in those containing both PEG and HA. There were no significant differences in cell morphology between any of the hydrogel compositions or medium formulations.

Alcian Blue staining for the deposition of glycosaminoglycans (GAG) was used as a marker of chondrogenic differentiation. Due to the background staining of the hydrogels (and particularly those containing HA), positive staining was determined to be any area more intense than the overall background matrix. Little GAG deposition was observed by cells encapsulated in either the PEG or PEG/HA gels, even in the presence of chondrogenic supplements. However, there were many areas of intense Alcian blue staining both surrounding, and between, diPSC-MSCs in PEG/HA+HA-PPS gels in the presence of chondrogenic supplements being strongly suggestive of chondrogenic differentiation. Conversely, whilst there was an abundance of Alizarin Red-positive deposits in the PEG hydrogels cultured in osteogenic medium, differentiation was significantly reduced in the PEG/HA and HA-PPS hydrogels.

These results show that canine iPSCs can be used to efficiently generate MSCs that are highly proliferative, express MSC and pluripotency markers and undergo robust osteo-, chondro- and adipogenesis. It has also been shown that when incorporated into hydrogels containing pentosan polysulphate in the form of HA-PPS, these iPSC-derived MSCs are stimulated to differentiate along the chondrogenic pathway, providing a first step in the process towards developing an effective MSC-based therapy for osteoarthritis.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

TABLES

TABLE 1

Rheological characterisation of PEG/HA hydrogels incorporating soluble PPS and HA - PPS.

| Gel type | Cross-linker 1 (U/ml) | Cross-linker 2 (mM) | SP (ug/ml) | Time to 1 kPa (sec) | G' at 5000 sec (Pa) | G''at 5000 sec (Pa) | Critical Strain (%) |
|---|---|---|---|---|---|---|---|
| 2.5 mM alone | 0.25 | 2.5 | 0 | 475 | 5554 | 18.0 | 4.4 |
| 4 mM alone | 0.25 | 4.0 | 0 | 552 | 3992 | 2.4 | 13.0 |
| 2.5 mM + sol PPS | 0.25 | 2.5 | 5 | 501 | 5463 | 12.2 | 4.0 |
| 4 mM + sol PPS | 0.25 | 4.0 | 5 | 616 | 3470 | 2.3 | 9.8 |
| 2.5 mM + HA-PPS | 0.25 | 2.5 | 5 | 399 | 4641 | 23.9 | 10.1 |

BIBLIOGRAPHY

[1] Chen F H, Tuan R S: Mesenchymal stem cells in arthritic diseases. *Arthritis Res Ther* 2008, 10:223

[2] Spagnoli A, Longobardi L, O'Rear L: Cartilage disorders: potential therapeutic use of mesenchymal stem cells. *Endocr Dev* 2005, 9:17-30.

[3] Jorgensen C, Djouad F. Bouffi C, Mrugala D, Noel D: Multipotent mesenchymal stromal cells in articular diseases. *Best Pract Res Clin Rheumatol* 2008, 22:269-284.

[4] Noth U, Steinert A F, Tuan R S: Technology insight: adult mesenchymal stem cells for osteoarthritis therapy. *Nat Clin Pract Rheumatol* 2008, 4:371-380

[5] Tuan R S, Boland G, Tuli R: Adult mesenchymal stem cells and cell based tissue engineering. *Arthritis Res Ther* 2003, 5:32-45

[6] Shi S, Gronthos S: Perivascular niche of postnatal mesenchymal stem cells in human bone marrow and dental pulp. *J Bone Miner Res* 2003, 18:696-704.

[7] Gronthos S., McCarty R, Mrozik K, Fitter S, Paton S, Menicanin D, Itescu S, Bartold P M, Xian C. Zannettino A C: Heat shock protein-90 beta (Hsp90ss) is expressed at the surface of multipotential mesenchymal precursor cells (MPC) generation of a novel monoclonal antibody, STRO-4, with specificity for MPC from human and ovine tissues, *Stem Cells Dev* 2009, 18:1253-1262.

[8] Ghosh P, Wu J, Shimmon S, Zannettino A, Gronthos S, Itescu S: Pentosan polysulfate promotes proliferation and chondrogenic differentiation of adult human bone marrow derived mesenchymal precursor cells. *Arthritis Research & Therapy* 2010, 12:R28

[9] Chen Y S, R A Pelekanos, R L Ellis, R Home, E L Wolvetang and N M Fisk, (2012). Small molecule mesengenic induction of human induced pluripotent stem cells to generate mesenchymal stem/stromal cells. Stem Cells Translational Medicine 1:83-95.

The invention claimed is:

1. A conjugate compound comprising hyaluronic acid, or a salt or derivative thereof, covalently bonded to pentosan polysulfate, or a salt or derivative thereof; wherein the conjugate compound is of formula (I):

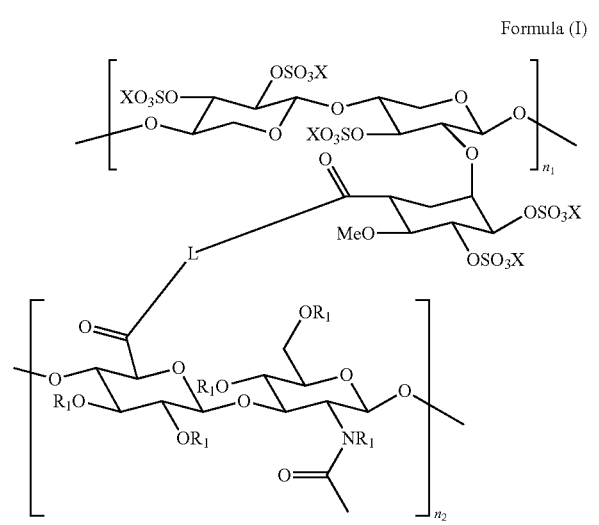

Formula (I)

wherein $n_1$ is sufficient to provide a molecular weight of between 1,000 to 20,000 daltons for the pentosan polysulfate component of the conjugate and $n_2$ is sufficient to provide a molecular weight of between 5,000 to 20,000,000 daltons for the hyaluronic acid component of the conjugate;

each X is independently a salt forming ion selected from the group consisting of sodium, calcium, magnesium and potassium ions or X may be selected from the group consisting of hydrogen, alkyl, alkenyl, carboxyl, alkanoyl, alkanoyloxy and carboalkoxy;

each $R_1$ group is independently selected from the group consisting of a salt forming ion, hydrogen, alkyl, alkenyl, arylalkyl, hydroxyalkyl, aldehyde, alkanone, carboxyl, carboxamide, alkanoyl, carboalkoxy, carboaryloxy, carbonate, O-alkyl, O-aryl, O-alkenyl, O-alkanoyl and O-alkenoyl; and L is a linker unit having a first reactive group reactive with a first complementary group on hyaluronic acid and having a second reactive group reactive with a second complementary group on pentosan polysulfate.

2. The conjugate compound of claim 1 wherein the first reactive group of the linker unit is reactive with a carbonyl or hydroxyl functional group on hyaluronic acid and the second reactive group of the linker unit is reactive with a carboxylic acid group on pentosan polysulfate.

3. The conjugate compound of claim 2 wherein the first and second reactive group are selected from the group consisting of $NH_2$, OH and SH.

4. The conjugate compound of claim 2 wherein L is formed from a $C_1$-$C_{20}$ alkyl diamine which reacts at the amine functionalities to bind to both HA and PPS, or derivatives thereof.

5. The conjugate compound of claim 1 wherein L is formed from $R_2$ which is selected from the group consisting of alkyl, aminoalkyl, diaminoalkyl, acyl and ether each of which may contain one or more heteroatoms selected from the group consisting of sulphur, oxygen and nitrogen.

6. The conjugate compound of claim 1 wherein $n_1$ is sufficient to provide a molecular weight of between 2000 to 10,000 daltons for the pentosan polysulfate component of the conjugate compound and $n_2$ is sufficient to provide a molecular weight of between 50,000 daltons to 2,000,000 daltons for the hyaluronic acid component of the conjugate.

7. The conjugate compound of claim 1 wherein the conjugate compound of formula (I) is a conjugate compound of formula (II):

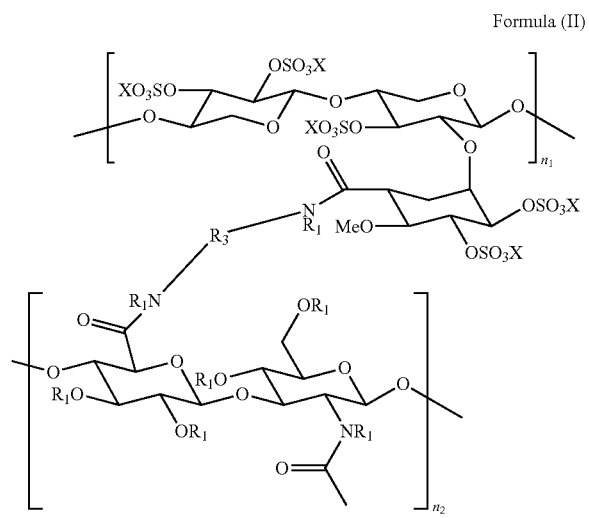

Formula (II)

wherein X, $R_1$, $n_1$ and $n_2$ are as previously defined and wherein, $R_3$ is selected from the group consisting of alkyl, disulphide, alkyldisulphide, acyl, ether, carboalkoxy and alkanoyloxy.

8. The conjugate compound of claim 7 wherein the conjugate compound of formula (II) is a conjugate compound of formula (III), or a salt thereof:

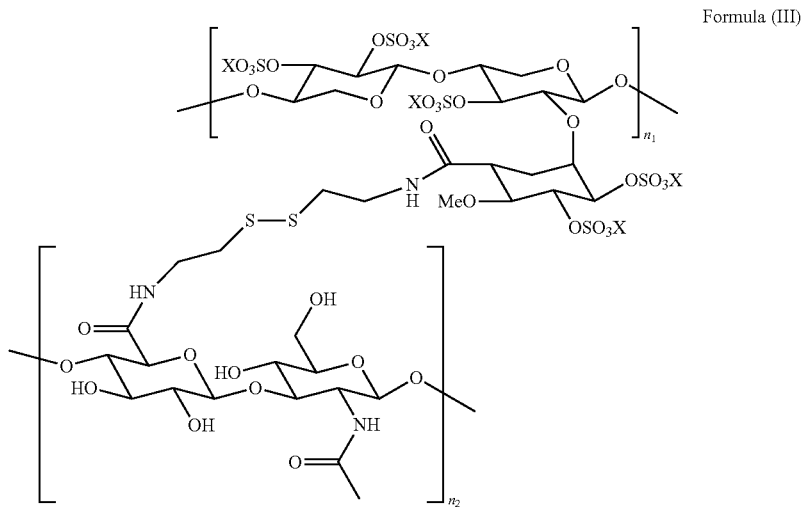

Formula (III)

wherein $n_1$ and $n_2$ and X are as previously defined.

9. The conjugate compound of claim 7 wherein the conjugate compound of formula (II) is a conjugate compound of formula (IIIa), or a salt thereof:

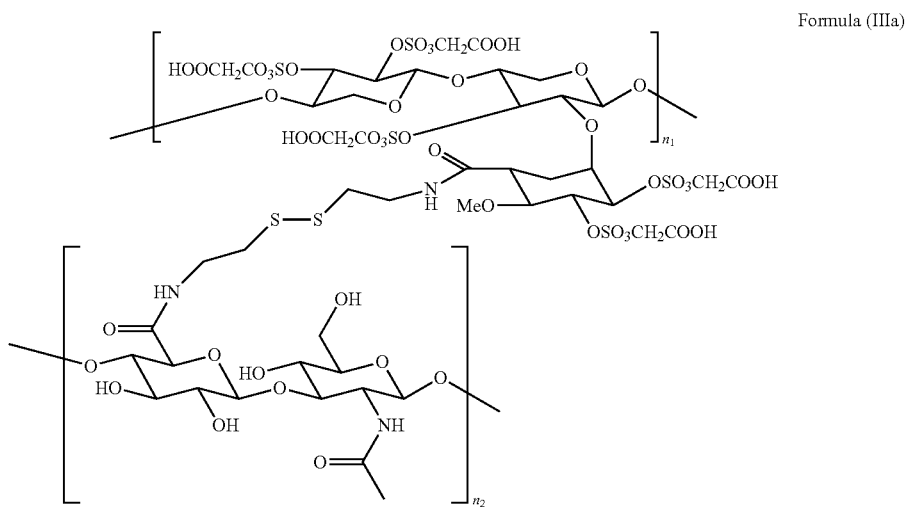

Formula (IIIa)

wherein $n_1$ and $n_2$ are as previously defined.

10. A pharmaceutical composition comprising an effective amount of a conjugate compound of claim 1 and a pharmaceutically acceptable carrier, diluent and/or excipient.

11. The composition of claim 10 further comprising a pluripotent or multipotent stem cell population.

12. The composition of claim 11 comprising a polymeric matrix within which the conjugate compound and stem cell population are captured.

13. A method of treating a disease, disorder or condition responsive to connective tissue repair and/or maintenance in a patient including the step of administering an effective amount of the conjugate compound of claim 1 and a pluripotent or multipotent stem cell population, and/or progeny cells thereof, to the affected or potentially affected tissue.

14. The method of claim 13 wherein the disease, disorder or condition is connective tissue degeneration.

15. The method of claim 13 wherein the affected tissue is an intervertebral disc, a cartilaginous structure or bone tissue.

16. The method of claim 13 wherein the conjugate compound and stem cell population are co-administered within a polymeric matrix.

17. The method of claim 13 further comprising administering an additive selected from the group consisting of glycosaminoglycan (GAG), unbound hyaluronic acid (HA), chondroitin sulphate, dermatan sulphate, keratin sulphate, heparin, heparin sulphate and unbound PPS.

18. A method of enhancing, promoting or maintaining the chondrogenic potential of a stem cell including the step of contacting the stem cell with a conjugate compound of claim 1.

19. A method of reducing or inhibiting the osteogenic differentiation of a stem cell including the step of contacting the stem cell with a conjugate compound of claim 1.

* * * * *